United States Patent [19]
Kopchick et al.

[11] Patent Number: 5,350,836
[45] Date of Patent: Sep. 27, 1994

[54] GROWTH HORMONE ANTAGONISTS

[75] Inventors: John J. Kopchick; Wen Y. Chen, both of Athens, Ohio

[73] Assignee: Ohio University, Athens, Ohio

[21] Appl. No.: 878,703

[22] Filed: May 4, 1992

Related U.S. Application Data

[63] Continuation-in-part of Ser. No. 693,305, May 1, 1991, abandoned, which is a continuation-in-part of Ser. No. 419,561, Oct. 12, 1989, abandoned.

[51] Int. Cl.$^5$ .................. C07K 13/00; C12P 21/06; A61K 37/36
[52] U.S. Cl. .................................. 530/399; 435/69.4
[58] Field of Search ...................... 530/399; 435/69.4

[56] References Cited

U.S. PATENT DOCUMENTS

| | | |
|---|---|---|
| 3,664,925 | 5/1972 | Sonenberg et al. . |
| 4,056,520 | 11/1977 | Sonenberg et al. . |
| 4,443,539 | 4/1984 | Fraser et al. . |
| 5,079,345 | 1/1992 | Becker et al. . |

FOREIGN PATENT DOCUMENTS

| | | |
|---|---|---|
| PCT/US90/-05874 | 10/1990 | World Int. Prop. O. . |
| PCT/US90/-03550 | 1/1991 | World Int. Prop. O. . |
| 9100870 | 1/1991 | World Int. Prop. O. . |
| PCT/US92/-03743 | 5/1992 | World Int. Prop. O. . |

OTHER PUBLICATIONS

Chou and Fasman, Prediction of protein conformation, Biochemistry 13:222-245, 1974.
DeGrado et al., Kinetics and mechanism of hemolysis induced by melittin and by a synthetic melittin analogue, Biophys J 37:329-338, 1982.
Fuh et al., Rational design of potent antagonists to the human growth hormone receptor, Science 256:1677-1680, 1992.
Hara et al., Recombination of the biologically active peptides from a tryptic digest of bovine growth hormone, Biochem 17(3):550-556, 1978.
McGrane et al., J Biol Chem 263:11443-11451, 1988.
Paladini et al., The intriguing nature of the multiple actions of growth hormone TIBS 256:256-260, 1979.
Smith and Talamantes, Identification and characterization of heterogeneous population of growth hormone receptors . . . , J Biol Chem 262:2213-2219, 1987.
Sporn et al., Transforming growth factor-$\beta$: biological function and chemical structure, Science 233:532-534, 1986.
Swislocki et al, In vitro metabolic effects of bovine growth hormone fragments in adipose tissue, Endocrinology 87(5):900-904, 1970.
Yamasaki et al., Studies on the common active site of growth hormone, Revision of the amino acid sequence of an active fragment of bovine growth hormone, J Biol Chem 250(7):2510-2514, 1975.
Zoller and Smith, Methods Enzymol 154:329-350, 1987.
Brems et al., Biochemistry, 26:7774 (1987) Helical Formation in Isolated Fragments of Bovine Growth Hormone.
Chen and Sonenberg, J. Biol. Chem., 250:2510-14 (1977) Revision of the Amino Acid Sequence of an Active Fragment of Bovine Growth Hormone.
Hammer, et al., Nature, 315:680-683 (1985) Production (List continued on next page.)

*Primary Examiner*—Garnette D. Draper
*Assistant Examiner*—Karen Cochrane Carlson
*Attorney, Agent, or Firm*—Pennie & Edmonds

[57] ABSTRACT

The present invention relates to antagonists of vertebrate growth hormones obtained by mutation of the third alpha helix of such proteins (especially bovine or human GHs). These mutants have growth inhibitory or other GH-antagonizing effects. These novel hormones may be administered exogenously to animals, or transgenic animals may be made that express the antagonist. Animals have been made which exhibited a reduced growth phenotype.

27 Claims, 12 Drawing Sheets

OTHER PUBLICATIONS of Transgenic Rabbits, Sheep and Pigs by Microinjection.

Kopchick et al., Brazil. J. Genetics, 12:37–54 (1989).

Kaiser, "Design of Amphiphilic Peptides, Protein Engineering 193–199" (Oxender and Fox, eds., 1987).

DeGrado et al., J. Am. Chem. Soc, 103:679 (1981) Design, Synthesis and Characterization of a Cytotoxic Peptide with Melittin–Like Activity.

Chen, et al., "Expression of a mutated bovine growth hormone gene suppresses growth of transgenic mice," Proc. Natl. Acad. Sci. 87:5061–65, Jul. 1990.

Brems, et al., "Stabilization of an associated folding intermediate of bovine growth hormone by site-directed mutagenesis," Proc. Natl. Acad. Sci. 85:3367–3371, May 1988.

Tou, et al., "Amphiphilic growth hormone releasing factor (GRF) analog: peptide design and biological activity invivo," Biochem. and Biolphys. Res. Comm., vol. 139, No. 2, pp. 763–770, Sep. 16, 1986.

Alan R. Liss Inc., "Protein Engineering", pp. 193–199, 1987.

Cunningham, et al., "Receptor and Antibody Epitopes in Human Growth Hormone Identified by Homolog-Scanning Mutagenesis," Science, 243:1330–1336, Mar. 10, 1989.

Hammer, et al., "Production of transgenic rabbits, sheep and pigs by microinjection," Nature, 315:680–683, Jun. 20, 1985.

Palmiter, et al., "Dramatic growth of mice that develop from eggs microinjected with metallothionein-growth hormone fusion genes," Nature, 300:611–615, Dec. 16, 1982.

Palmiter, et al., "Metallothionein-Human GH Fusion Genes Stimulate Growth of Mice," Science, 222:809–814, Nov. 18, 1983.

Chen, X., et al., "Conversion of Bovine Growth Hormone Cysteine Residues to Serine Affects Secretion by Cultured Cells and Growth Rates in Transgenic Mice", Mol. Endo. 6:598–606 (1992).

Chen et al., "Functional Antagonism between Endogenous Mouse Growth Hormone (GH) and a GH Analog Results in Dwarf Transgenic Mice", Endo. 129: 1402–1408 (1991).

Chen et al., "Glycine 119 if Bovine Growth Hormone is Critical for Growth Promoting Activity," Mol. Endo. 5: 1845–1852 (1991).

Chen et al., "Mutations in the Third α-Helix of Bovine Growth Hormone Dramatically Affect Its Intracellular Distribution in Vitro and Growth Enhancement in Transgenic Mice," J. Biol. Chem. 266: 2252–2258 (1991).

Chen et al., "Receptor Binding Mitogenic Activity and Transgenic Mouse Studies on bGH–hGH Analogs", Faseb J. 6 (4):A1344 (Apr. 5–9, 1992).

Chen et al., "Substitution Mutations at Lysine-64 (K64) of Bovine Growth Hormone (bGH) Affect Receptor Binding Affinities and Growth Rates of Transgenic Mice", Faseb J. 5 (4): A424 (Apr. 514 9, 1992).

Cunningham et al., "High Resolution Epitope Mapping of hGH–Receptor Interactions by Alanine Scanning Mutagenesis," Science 24: 1081–1085 (1989).

Goeddel et al., "Direct Expression in Escherichia Coli of a DNA Sequence Coding for Human Growth Hormone," Nature, 281: 544–548 (1979).

Kopchick and Cioffi, "Exogenous and Endogenous Effects of Growth Hormone in Animals", Livest. Prod. Sci. 27: 61–75 (1991).

McAndrews et al., "Effects of a Leucine Analog on Growth Hormone Processing and Secretion by Cultured Cells", J. Biol. Chem. 266: 15016–15020 (1991).

McAndrew et al., "Expression of Truncated Forms of the Bovine Growth Hormone Gene in Cultured Mouse Cells", J. Biol. Chem. 266: 20956–20969 (1991).

Okada, et al., "A Growth Hormone (GH) Analog Can Antagonize the Ability of Native GH to Promote Differentiation of 3T3–F442–A Preadipocytes and Stimulate Insulin–Like and Lipolytic Activities in Primary Rate Adipocytes", Endo, 2284–2290 (1992).

Okada et al., "Antagonism of Bovine Growth Hormone (bGH) Stimulated Glucose-Transport by a bGH Analog in 3T3–F442A Adipose Cells", Faseb J. 6 (4):PA 1272 (Apr. 5–9, 1992).

Parks et al., "Structural-Function Studies of the First Alpha–Helix of Bovine Growth Hormone", Faseb J. 6 (4): A1345 (1992).

Seeburg et al., "Efficient Bacterial Expression of Bovine and Porcine Growth Hormones," DNA 2(1):37–45 (1983).

Watahiki, M. et al., "Conserved and Unique Amino Acid Residues in the Domains of the Growth Hormones," J. Biol. Chem. 264: 312–316 (1989).

```
ATGATGGCTGCAGGCCCCCGGACCTCCCTGCTCCTGGCTTTCGCCCTGCTCTGCCTGCCC
 M  M  A  A  G  P  R  T  S  L  L  A  F  A  L  L  C  L  P
      -20                                           10
                    I————————————————————————————————————
TGGACTCAGGTGGTGGGCGCCTTCCCAGCCATGTCCTTGTCCGGCCTGTTTGCCAACGCT
 W  T  Q  V  V  G  A  F  P  A  M  S  L  S  G  L  F  A  N  A
———————— Helix I ——————————————————————————————————————————I
GTGCTCCGGGCTCAGCACCTGCATCAGCTGGCTGCTGACACCTTCAAAGAGTTTGAGCGC
 V  L  R  A  Q  H  L  H  Q  L  A  A  D  T  F  K  E  F  E  R
             20                                  30
ACCTACATCCCGGAGGGACAGAGATACTCCATCCAGAACACCCAGGTTGCCTTCTGCTTC
 T  Y  I  P  E  G  Q  R  Y  S  I  Q  N  T  Q  V  A  F  C  F
             40                                  50
                              I————————————— Helix II————
TCTGAAACCATCCCGGCCCCCACGGGCAAGAATGAGGCCCAGCAGAAATCAGACTTGGAG
 S  E  T  I  P  A  P  T  G  K  N  E  A  Q  Q  K  S  D  L  E
             60                                  70
——————————————I
CTGCTTCGCATCTCACTGCTCCTCATCCAGTCGTGGCTTGGGCCCCTGCAGTTCCTCAGC
 L  L  R  I  S  L  L  L  I  Q  S  W  L  G  P  L  Q  F  L  S
             80                                  90
                                 I————————————————————————
AGAGTCTTCACCAACAGCTTGGTGTTTGGCACCTCGGACCGTGTCTATGAGAAGCTGAAG
 R  V  F  T  N  S  L  V  F  G  T  S  D  R  V  Y  E  K  L  K
            100                                 110
———— Helix III——————————————I
GACCTGGAGGAAAGGATCCTGGCCCCTGATGCGGGAGCTGGAAGATGGCACCCCCCGGGCT
 D  L  E  E  R  I  L  A  L  M  R  E  L  E  D  G  T  P  R  A
            120                                 130
                                        I——————————————————
GGGCAGATCCTCAAGCAGACCTATGACAAATTTGACACAAACATGCGCAGTGACGACGCG
 G  Q  I  L  K  Q  T  Y  D  K  F  D  T  N  M  R  S  D  D  A
            140                                 150
————————————————————————— Helix IV ————————————————————
CTGCTCAAGAACTACGGTCTGCTCTCCTGCTTCCGGAAGGACCTGCATAAGACGGAGACG
 L  L  K  N  Y  G  L  L  S  C  F  R  K  D  L  H  K  T  E  T
            160                                 170
——————————————I
TACCTGAGGGTCATGAAGTGCCGCCGCTTCGGGGAGGCCAGCTGTGCCTTCTAG
 Y  L  R  V  M  K  C  R  R  F  G  E  A  S  C  A  F  END
            180                                 190
```

FIG.1

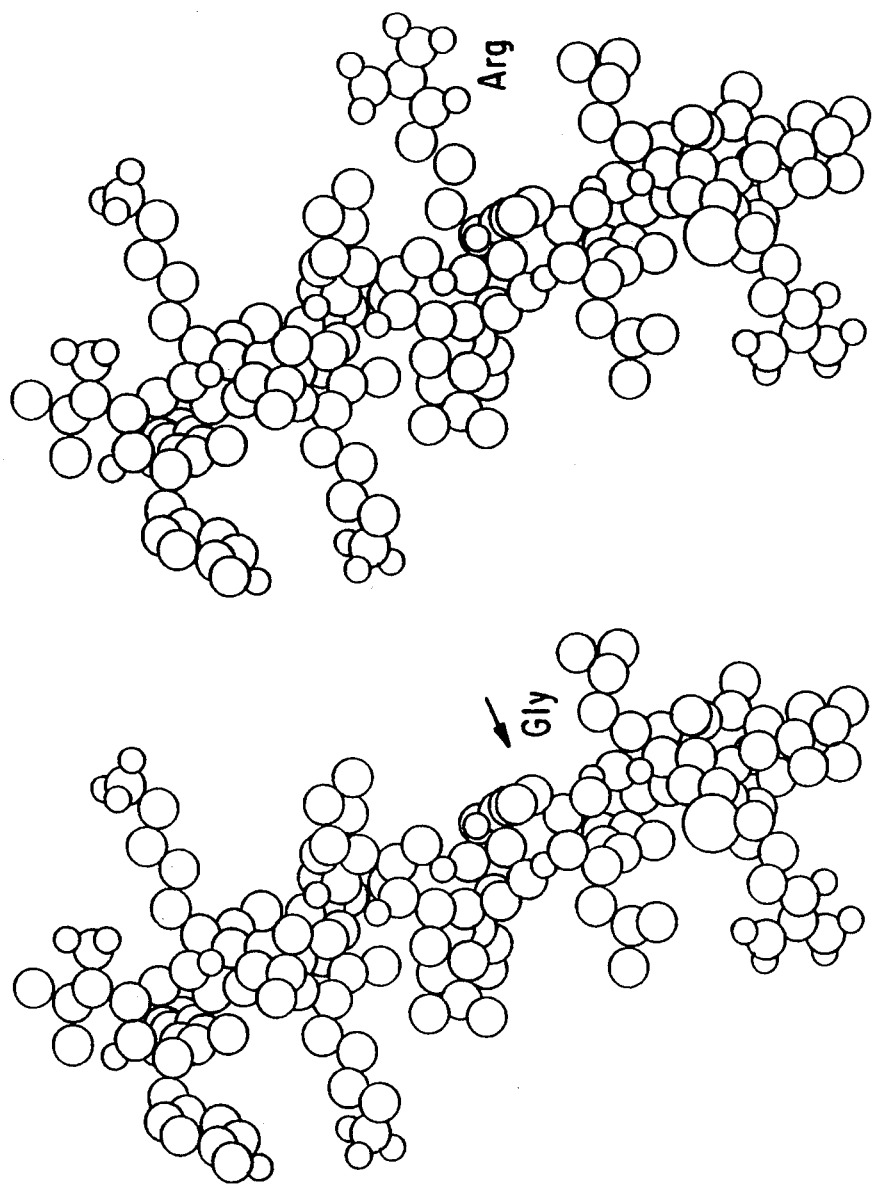

GROWTH HORMONE ANTAGONISTS

This application is a continuation-in-part of U.S. Ser. No. 07/693,305, filed May 1, 1191, abandoned, which is a continuation-in-part of PCT/US90/05874, filed Oct. 12, 1990, abandoned, which is a continuation-in-part of U.S. Ser. No. 07/419,561, filed Oct. 12, 1989, abandoned, all of which are hereby incorporated by reference herein.

BACKGROUND OF THE INVENTION

1. Field of the Invention

This invention relates to novel growth hormone, especially bovine growth hormone, muteins which inhibit the growth of animals or otherwise antagonize the effects of endogenous growth hormone. These analogues may be expressed in transgenic animals which thereby acquire a "reduced growth" phenotype.

2. Information Disclosure Statement

Bovine growth hormone (GH) is a protein of 191 amino acids that is naturally synthesized in the anterior pituitary. The molecular weight of the mature protein is about 22,000 daltons, but it is initially made as a pregrowth hormone with an extra 26 amino acids on the amino terminal. This leader (or signal peptide) is normally cleaved during secretion of the hormone by bovine pituitary cells. Several forms of the mature protein have been found in nature. The N-terminal can vary (due to variation in the site of cleavage during secretion) so that the mature protein begins with either $NH_2$-Ala-Phe-Pro or $NH_2$-Phe-Pro. Additionally, the amino acid at position 126 may be either leucine or valine, apparently as a result of allelic variation in the bovine population.

Exogenous administration of bGH to cattle increases milk production, feed efficiency, growth rate, and the lean-to-fat ratio, and decreases fattening time.

bGH has been produced by recombinant DNA techniques, see e.g., Fraser, U.S. Pat. No. 4,443,539 (yeast; Buell, EP Appl. 103,395 (bacteria); Krivl, EP Appl. 193,515 (bacterial); Kopchick, EP Appl. 161,640 (encapsulated mouse cells implanted into animals); DeBoer, EP Appl. 75,444 (bacteria; gene modified to eliminate harmful secondary structure) and this has facilitated the production of analogues of bGH by site-specific mutagenesis. Thus, Aviv, GB 3,073,245 describes production of Met Pro (des Ala) bGH, Met Arg (des Ala) bGH, Met-Glu-Gly (des Ala) bGH, and des (Ala$^1$Phe$^2$-Pro$^3$-Ala$^4$) bGH in *E. coli*. Brems, et al., PNAS (USA) 85:3367–71 (1988) reported preparation of the bGH mutant K112L, which extended the hydrophobic face of the third alpha helix of bGH. The 96–133 fragment of this mutant was also prepared.

The biological activity of proteolytic fragments of bGH has also been studied. Brems, et al., Biochemistry, 26:7774 (1987); Swislocki, et al., Endocrinology, 87:900 (1970); Paladini, et al., TIBS, 256 (Nov. 1979). The fragment of bGH containing amino acids 96–133 is superior in growth promoting assays to bGH 1–95 and bGH 151–191. Hara, et al., Biochemistry, 17:550 (1978); Sonenberg, U.S. Pat. Nos. 3,664,925 and 4,056,520; Chen and Sonenberg, J. Biol. Chem., 250:2510–14 (1977). An octapeptide derived from the amino-terminal of hGH has been shown to have hypoglycemic activity, see Ng, et al., Diabetes, 23:943–949 (1974), but it has no effect on growth. Similar results were observed with the fragment bGH (96–133). Graf, et al., Eur. J. Biochem., 64:333–340 (1976); Hara, et al., Biochem., 17:550–56 (1978).

Analogues of bGH have varied in growth-promoting activity, as have the known analogues of other growth hormones. However, a growth hormone analogue having growth-inhibitory activity has not previously been reported.

A variety of transgenic animals have been produced. Hammer, et al., Nature, 315:680–683 (1985) (rabbits, sheep and pigs). Certain of these animals have been caused to express a growth hormone, and increased growth of such transgenic animals has been reported. Palmiter, et al., Nature 300:611 (1982) microinjected the male pronucleus of fertilized mouse eggs with a DNA fragment containing the promoter of the mouse metallothionein-I gene fused to the structural gene of rat growth hormone. Several of the transgenic mice developed from the genetically modified zygote exhibited a growth rate substantially higher than that of control mice. (In effect, the genetically modified mouse serves as a test environment for determining the effect of the hormone on animal growth). Later, Palmiter, et al., Science, 222:809 (1983) demonstrated that a similar enhancement of growth could be obtained in transgenic mice bearing an expressible human growth hormone gene. A like effect is observed when human growth hormone releasing factor is expressed in transgenic mice. Hammer, et al., Nature, 315:413 (1985).

Bovine growth hormone has also been expressed in transgenic animals. McGrane, et al. J. Biol. Chem., 263:1144351 (1988); Kopchick, et al., Brazil. J. Genetics, 12:37–54 (1989). However, transgenic animals characterized by an exogenous gene which confers a reduced growth phenotype were hitherto unknown.

SUMMARY OF THE INVENTION

The present invention relates to proteins which are substantially homologous with a vertebrate growth hormone but have growth-inhibitory activity.

We have discovered that mutation of Gly$^{119}$ inn bGH to Arg ("G119R"), Pro ("G119P"), Lys ("G119K"), Trp ("G119W") or Leu ("G119L"), or the homologous Gly$^{120}$ in hGH to Arg or Trp, results in a mutein (mutant protein or peptide fragment thereof) which has growth-inhibitory activity in vertebrates, especially mammals. This novel hormone may be administered to mammals (or other vertebrates), in particular humans and bovines, when growth inhibition is desirable.

In one embodiment of the invention, the hormone is produced exogenously and administered to the subject. In view of the size of the hormone, it is preferably produced by expression in a suitable host of a gene coding for it. Such a gene is most readily prepared by site-specific mutagenesis of a bGH gene. However, the hormone may also be produced by other techniques, such as by condensation of fragments of native bGH with a synthetic peptide carrying the replacement amino acid. If a peptide fragment has the desired growth-inhibitory activity, it may be prepared in toto by a Merrifield-type synthesis.

In a second embodiment of the invention, this gene is introduced into a prenatal form of a mammal by known techniques, and the prenatal form is developed into a transgenic mammal which expresses a reduced growth phenotype. Conceivably, a mammal could be genetically modified after birth, i.e., "gene therapy".

Thus, growth-inhibited animals may be produced either by administration of the growth inhibitory hormone of this invention in pharmaceutical form, or by genetic transformation of a prenatal or postnatal form of the animal.

The growth-inhibitory hormone, or the gene encoding it, is useful in the production of small animals for use in research facilities where space is restricted, as pets for pet lovers with limited quarters, and as livestock for farmers having small tracts. The hormone may also be useful in the treatment of human gigantism, and in research on gigantism and dwarfism, in the treatment of diabetes and its sequelae, in the control of cholesterol, and in the prevention and treatment of certain cancers.

Characteristically, patients with poorly controlled diabetes have been found to have high levels of circulating growth hormone. See, e.g., Lundbaek, et al., Lancet, 2:13–33 (1970). It has been speculated that high levels of growth hormone may contribute to poor diabetic control, as opposed to being merely a consequence thereof. Press, et al., New England J. Med., 310:810–14 (1984). Attempts have been made to inhibit growth hormone release by means of somatostatin analogues. However, use of growth hormone antagonists has not been reported previously. Thus, a further aspect of the present invention is the use of the disclosed GH antagonists to improve diabetic control.

Among the complications of diabetes are retinopathy, nephropathy and angiopathy. Diabetic retinopathy is believed to arise as a result of the proliferation of microvascular endothelial cells in the retina. Human growth hormone is known to stimulate proliferation of microvascular endothelial cells. See Rymaszewski, et al., Proc. Nat. Acad. Sci. USA 88:617–21 (1991). The growth hormone antagonists of the present invention may therefore be useful in countering the adverse effects of elevated levels of endogenous growth hormone on microvascular tissues, such as the retina, in diabetics, or in other individuals experiencing excessive growth hormone levels.

Glomerulosclerosis occurs in a variety of glomerular diseases, including diabetic nephropathy. The cause if unknown, but mesangial cell proliferation precedes or accompanies mesangial sclerosis. Thus, dysregulation of resident glomerular cells may be an important issue in the development of glomerulosclerosis (Doi, et al., Am. J. Pathol., 137:541, 1990).

Transgenic mice which express bGH have been shown to have enlarged glomeruli which progressed to a state of glomerulosclerosis. Thus, GH has been implicated in the development of diabetic glomerulosclerosis (Doi, et al., 1990 and Bell, Am. J. Med. Sci., 301:195, 1991). A GH antagonist could alleviate the GH-dependent effect on the cells of the diabetic kidney, and thereby be useful in the prevention of treatment of glomerulosclerosis.

While growth hormones have not previously been implicated in hypercholesterolemia, in another embodiment, GH antagonists are used to reduce serum cholesterol levels.

It has been suggested that long-activity somatostatin analogues may have value in the control of breast and prostate cancers. Manni, Biotherapy, 4:31–36 (1992). Manni hypothesizes that they could inhibit tumor growth by a number of mechanisms, including inhibiting growth hormone secretion. Growth hormone is implicated because it is lactogenic and because it elevates IGF-1 levels. We suggest that the growth hormone antagonists of the present invention may be used in the treatment of cancers whose growth is facilitated by endogenous growth hormone or IGF-1.

In general, these antagonists are therapeutically or prophylactically useful in countering the adverse effects of growth hormones, both endogenous hormones and hormones administered clinically.

In the course of our work, we have discovered a correlation between the ability of mouse L cells to secrete the protein and the protein having an effect (positive or negative) on growth rate in a transgenic animal. The use of an L cell secretion assay to identify growth-modulating proteins in also a part of this invention.

The appended claims are hereby incorporated by reference as a further enumeration of the preferred embodiments. All patents and publications cited in this specification are incorporated by reference.

BRIEF DESCRIPTION OF THE DRAWINGS

FIG. 1 Amino acid sequence of bGH (G119R) and nucleotide sequence of the gene encoding this analogue. The alpha helices are marked and the amino acids are numbered, with number 1 being the first amino acid of the mature protein. The boldfaced bases and amino acids are those mutagenized in the G119R mutant.

Hydrophobic amino acid sectors are shaded by dots: hydrophilic amino acids are indicated by open sectors; the glycine sector, a neutral amino acid, by slanted lines. The residue numbers and hydrophilicity values (Hopp and Wood scale) are given.

FIGS. 8A and 8B present side views of the third alpha helix of wild type (left) and G119R mutant (right) bGHs projected on the plane in which the side chain of the Arginine-119 of the mutant G119R lies. The glycine 119 residue found at the bottom of the cleft is indicated by an arrow.

The views were prepared by use of molecular modelling software (QUANTA and CHARMm, Polygene, Waltham, Massachusetts, (USA).

Figure 9A:
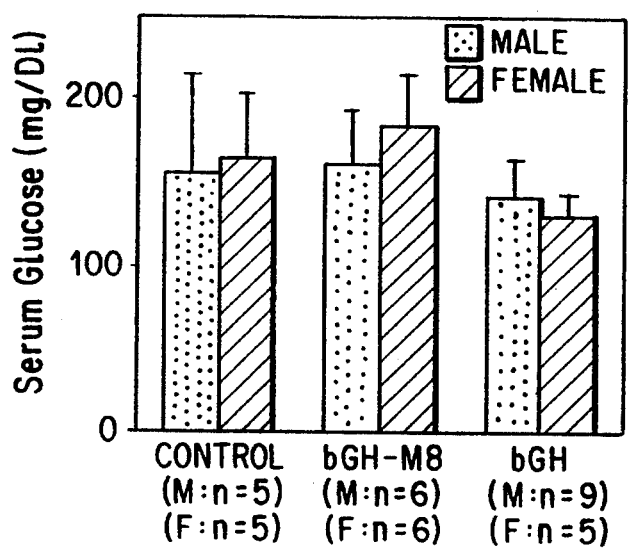
Figure 9B:
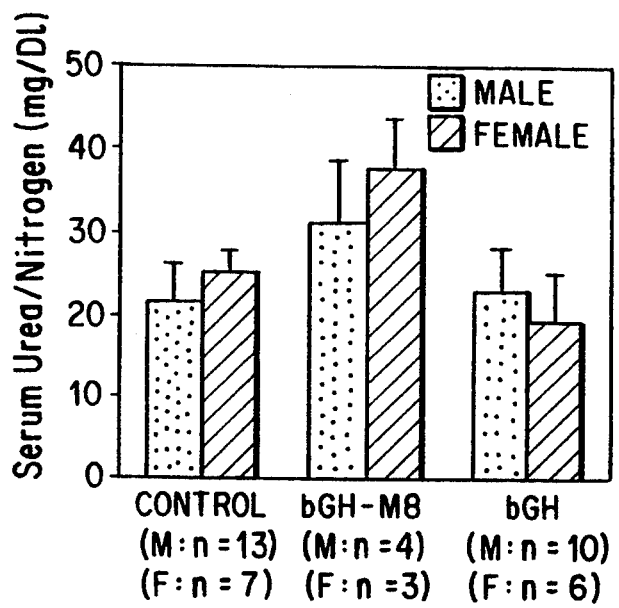
Figure 9C:
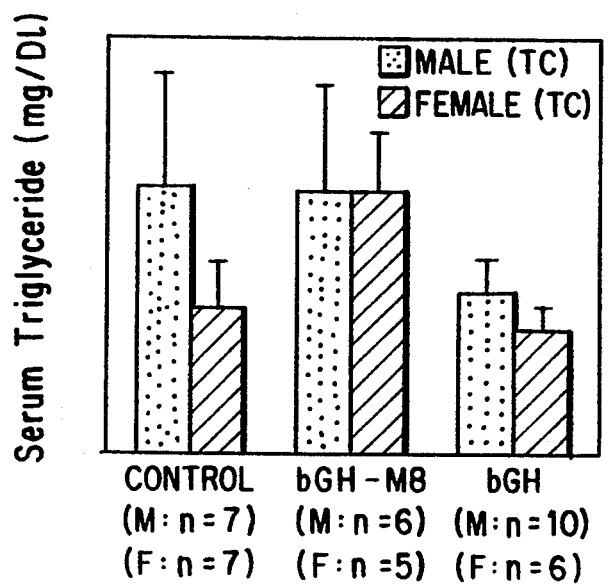

FIGS. 9A-9C compare serum glucose, urea/nitrogen, and triglyceride levels of control mice, transgenic bGH-M8 (E117L, G119R, A122D)-producing mice, and transgenic wtbGH-producing mice, of both sexes.

Figure 10:
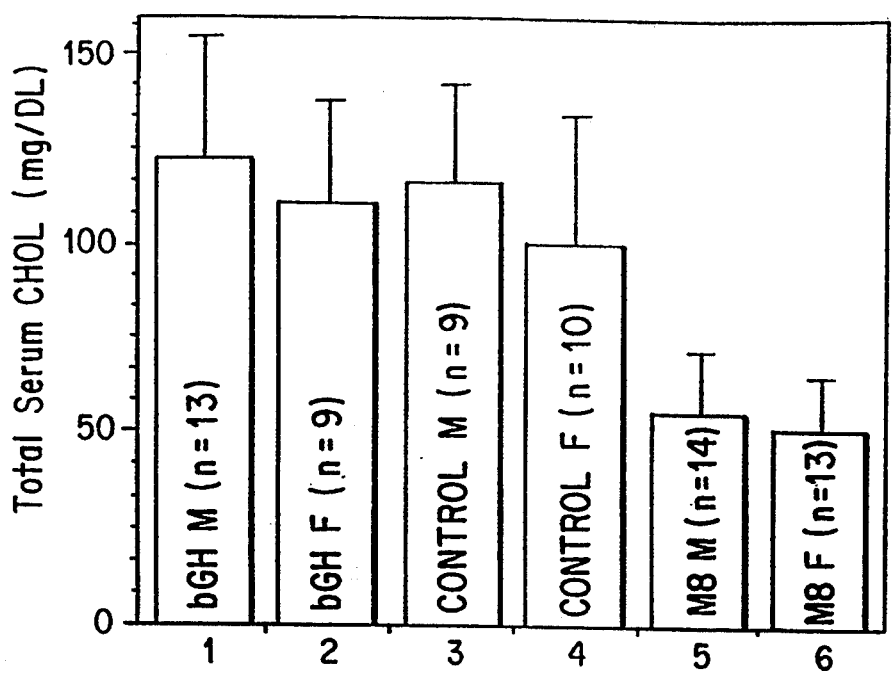

FIG. 10 compares serum cholesterol for transgenic wtbGH-producing mice, control mice, and transgenic bGH-M8-producing mice, of both sexes.

Figure 11:
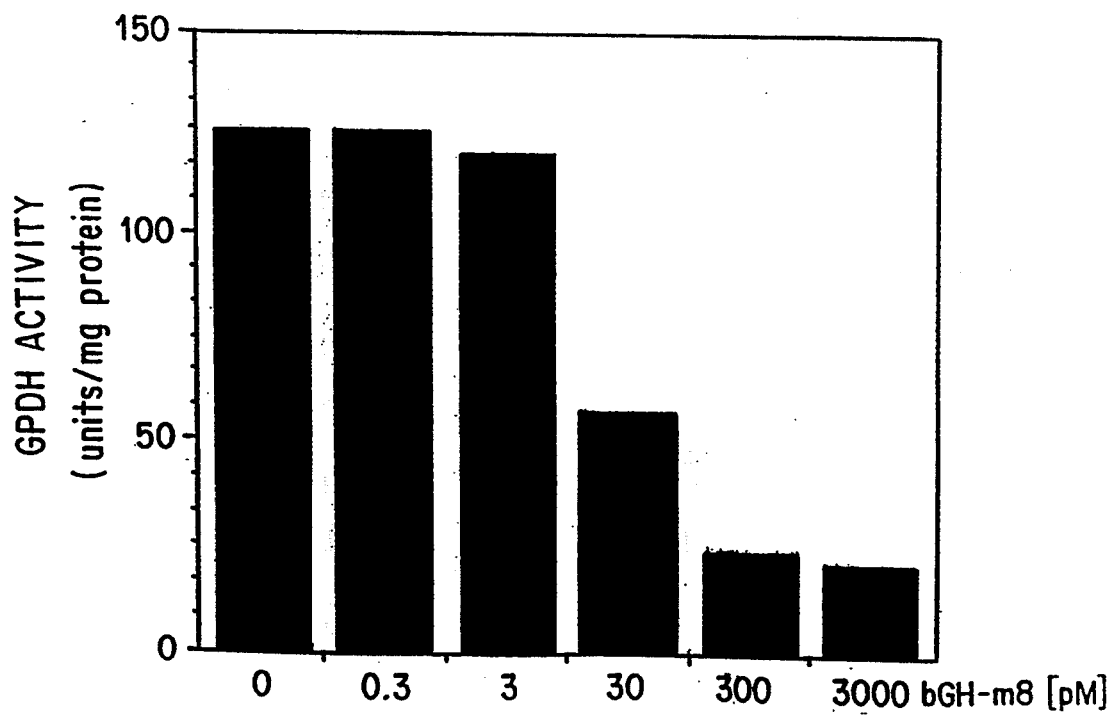

FIG. 11 plots GDPH activity against bGH-M8 dosage in a competitive inhibition assay for the antagonism of the ability of GH (here, wild-type bGH) to promote the differentiation of preadipocytes (NIH 3T3-F442A cells).

Figure 12:
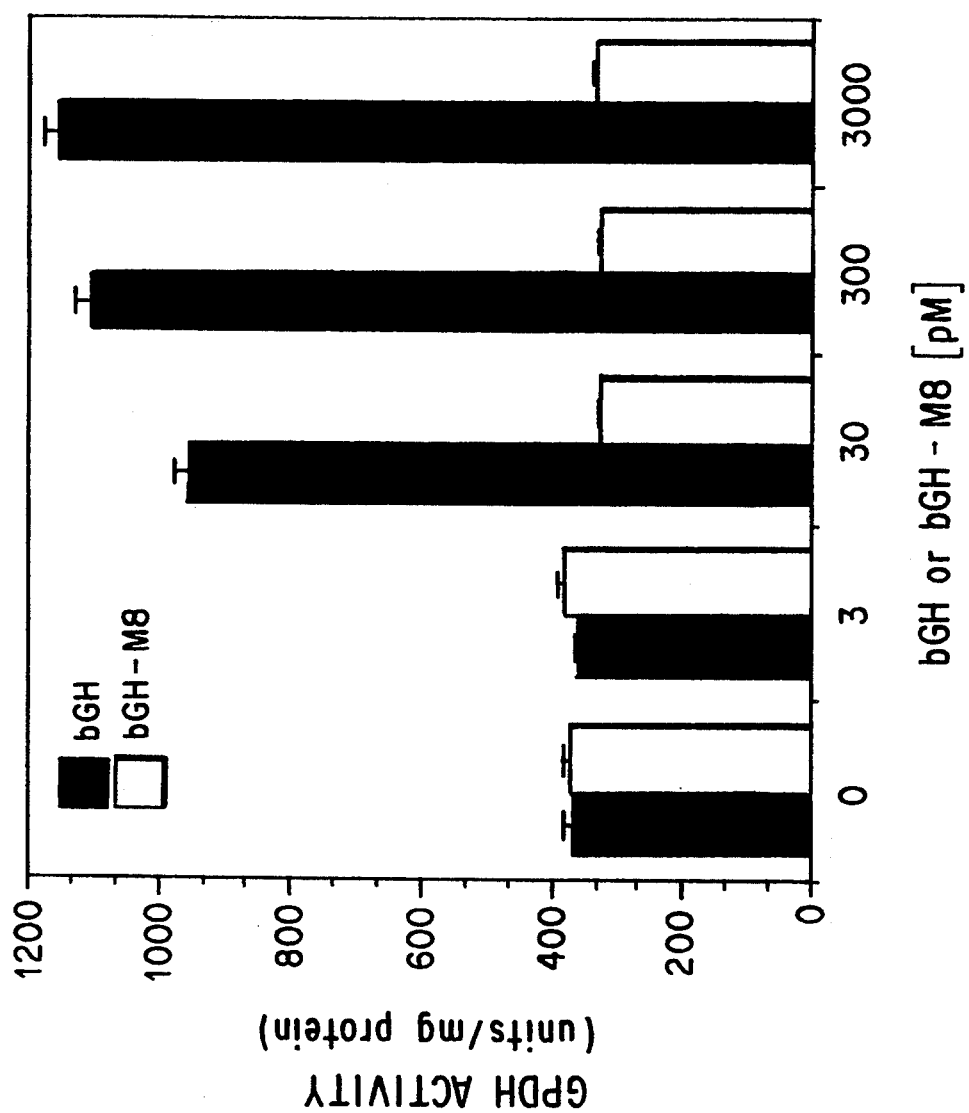

FIG. 12 compares of the effect of bGH and bGH-M8 on the differentiation of 3T3-F442A cells. At confluence, cells were incubated with increasing concentrations of bGH or Bgh-M8. Cells were harvested on day 8 for determination of GPDH activity. The experiment was repeated twice with similar results. Each bar represents the mean value obtained from triplicate assays. The error bar represents the standard division.

Figure 13:
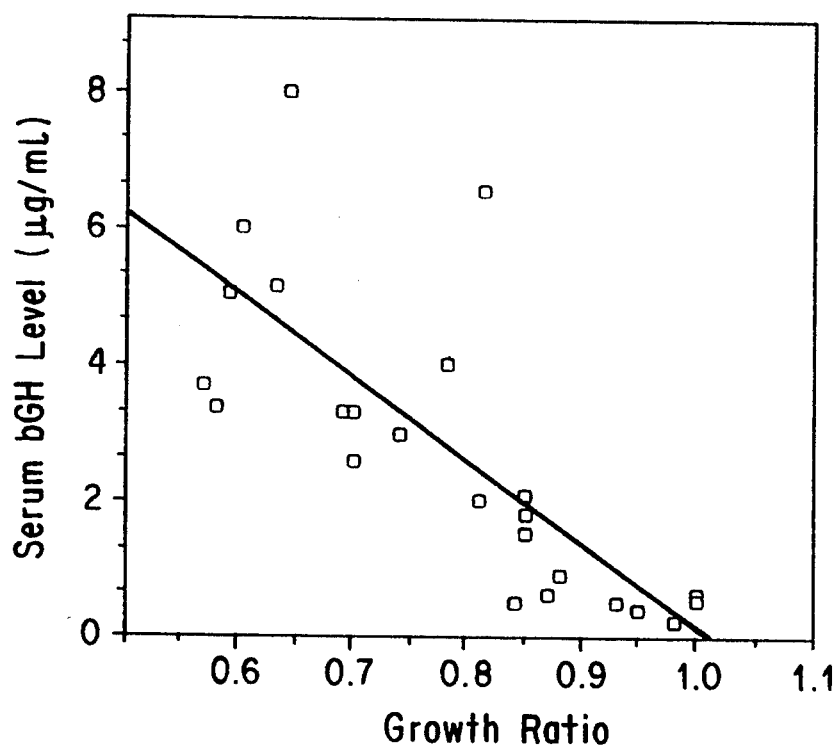

FIG. 13 shows the relationship between serum bGH analog concentrations and the growth ratio of transgenic mice (TG)/nontransgenic (NTG). The ordinate represents bGH analog concentrations in serum. The abscissa represents the growth ratio of TG/NTG mice.

Figure 14:
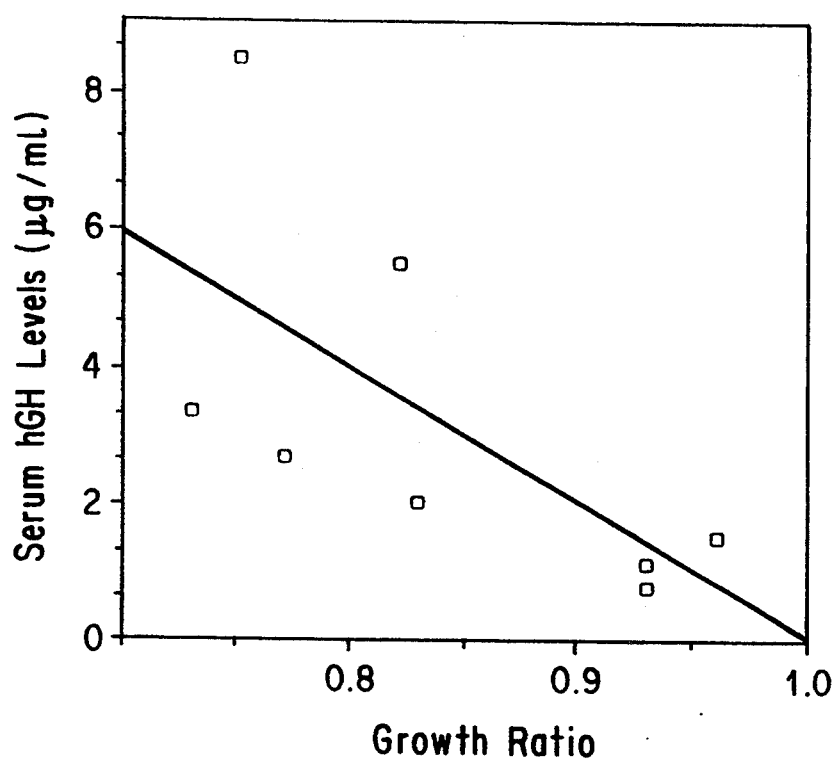

FIG. 14 shows the relationship between serum hGH analog concentrations and the growth ratio of transgenic mice (TG)/nontransgenic (NTG). The ordinate represents bGH analog concentrations in serum. The abscissa represents the growth ratio of TG/NTG mice.

DETAILED DESCRIPTION OF THE PREFERRED EMBODIMENTS

The present invention relates to growth hormone antagonists, especially growth inhibitors, which are peptides or proteins having a similarity in sequence and secondary structure to a vertebrate growth hormone, including but not limited to mammalian grown hormones, especially human and bovine growth hormones. Preferably, the compound comprises an alpha helix having an amino acid sequence homology of at least about 50% with the third alpha helix of a vertebrate growth hormone, especially bovine or human growth hormone. Other alpha helices of the native hormone may be omitted if this can be done without loss of growth-inhibitory and/or other growth hormone antagonist activity. The use of the term "antagonist" is in a functional sense and is not intended to limit the invention to compounds having a particular mechanism of action.

The overall percentage homology of bovine growth hormone with other mammalian growth hormones is high: porcine (92%), ovine (99%), human (66%), and rate (87%). Insofar as the third alpha helix (amino acid sequence homologous to bGH 109-126) is concerned, the percentage homology is comparable to the overall figure: porcine (94%), ovine (94%), human (66%), and rate (94%).

The secondary structure of a polypeptide is a regular arrangement of a linear segment of the polypeptide chain. The most commonly encountered secondary structures are the beta-sheets and the alpha-helices. See Schulz and Schimer, *Principles of Protein Structure* 69 (Springer-Verlag: 1979). The alpha helix is stabilized by hydrogen bonding between peptide amide and carbonyl groups of residues separated by a single turn of the helix. Secondary structure predictions are based on observation of the frequency of occurrence of the amino acid in a beta-sheet, alpha-helix, etc. in a protein having a known three dimensional structure.

The three-dimensional structure of porcine growth hormone has been determined by X-ray diffraction and compared to that of other growth hormones. Abdel-Meguid, et al., Proc. Nat. Acad. Sci., 84:6434(1987). Like the other growth hormones thus studied, it is a single domain protein arranged as a four helix bundle with the helices in an antiparallel relationship. Its four helixes are made up of residues 7-34, 75-87, 106-127 and 152-183. For X-ray studies of bGH and hGH, see Bell, et al., J. Biol. Chem., 260:8520-25 (1985) and DeVos, et al., Science, 255:306-312 (1992). The three-dimensional structures of other growth hormones may be deduced by comparison of the sequences with due regard for the secondary structure tendencies of substituted amino acids.

Bovine growth hormone is 92% homologous at the amino acid sequence level with porcine growth hormone, and bGH's structure has been deduced by study of the two sequences and of the structure of porcine growth hormone. Its four alpha helixes have been reported to be assumed by amino acids 4-33, 66-80, 108-127 and 150-179. The third alpha helix of bGH is defined as amino acids 160-129. However, it will be noted that the ends of this helix have a less marked alpha helical secondary structure than does the central region, which is 109-126. The exact bounds of the third alpha helix may differ for other GH's, depending on the alpha helical tendencies of the "end" amino acids. The conformation is reasonably consistent with the predictions made by Chen and Sonenber, Biochemistry, 16:2110 (1977) using the method of Chou and Fasman, Biochemistry, 13:222 (1974) (AAs 10-34, 66-87, 111-127, 186-191).

Figure 2:
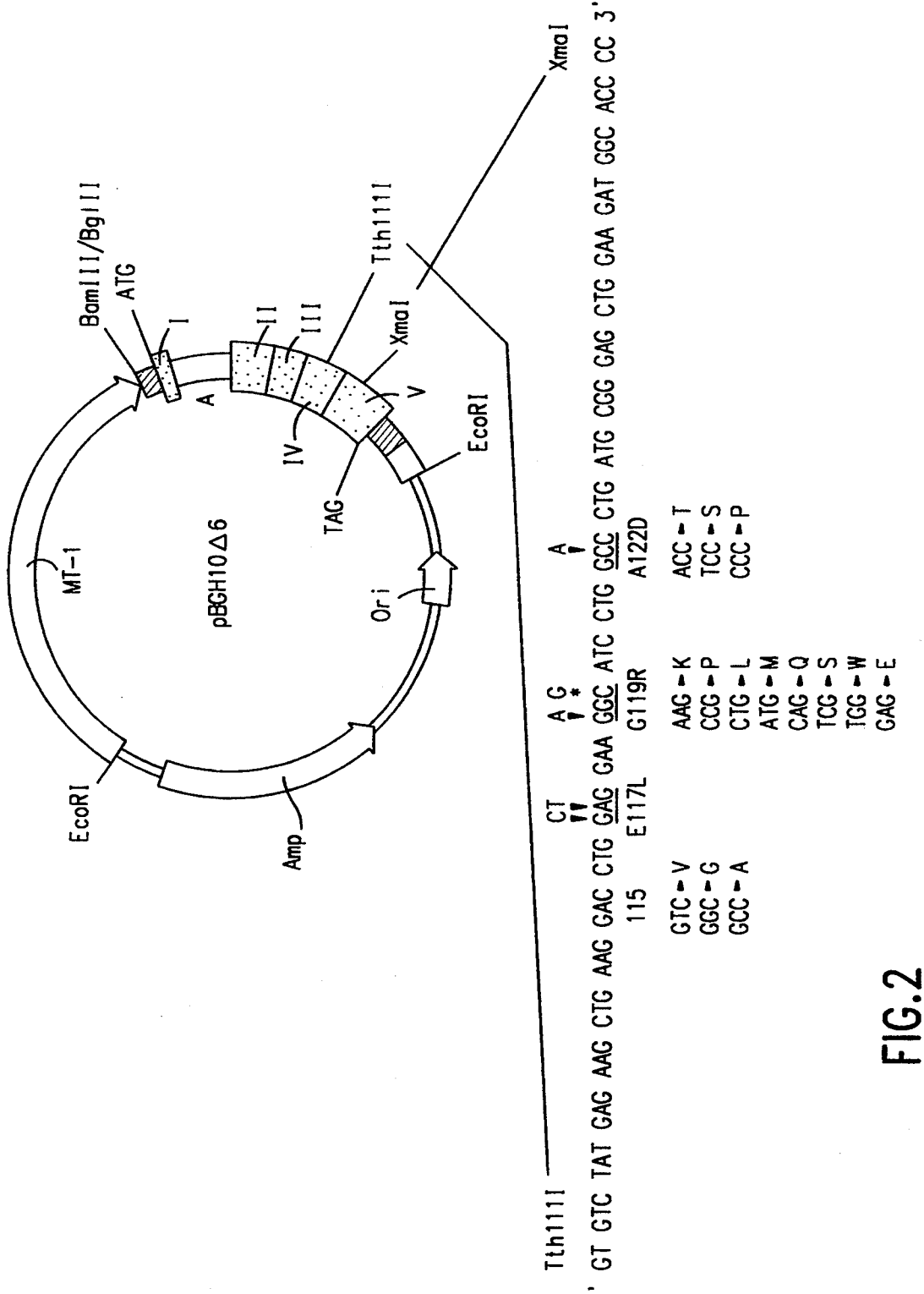
FIG. 2 General strategy of oligonucleotide directed mutagenesis. PBGH10Δ6 was used as the parental vector. It contains mouse metallothionein I transcriptional regulatory sequences (MT-1) fused to the bGH gene (BamHI joined with BglII) which contains five exons (shaded boxes I–V) and intron A. This fusion gene was incorporated into pBR322 at the EcoRI site. The pBR322 origin of replication (ORI), ampicillin resistant gene (Amp), as well as the bGH translation start (ATG) and stop (TAG) codons are indicated. 5' and 3' non-translated regions are shown in hatching. The nucleotide sequence between restriction sites TthlllI and XmaI is shown. Substitution mutations are indicated. One silent mutation is also indicated (*) which created a unique BamHI site. The position of the principal amino acid residues mutated in our experiments (115, 117, 119, 122) are indicated.
Figure 3:
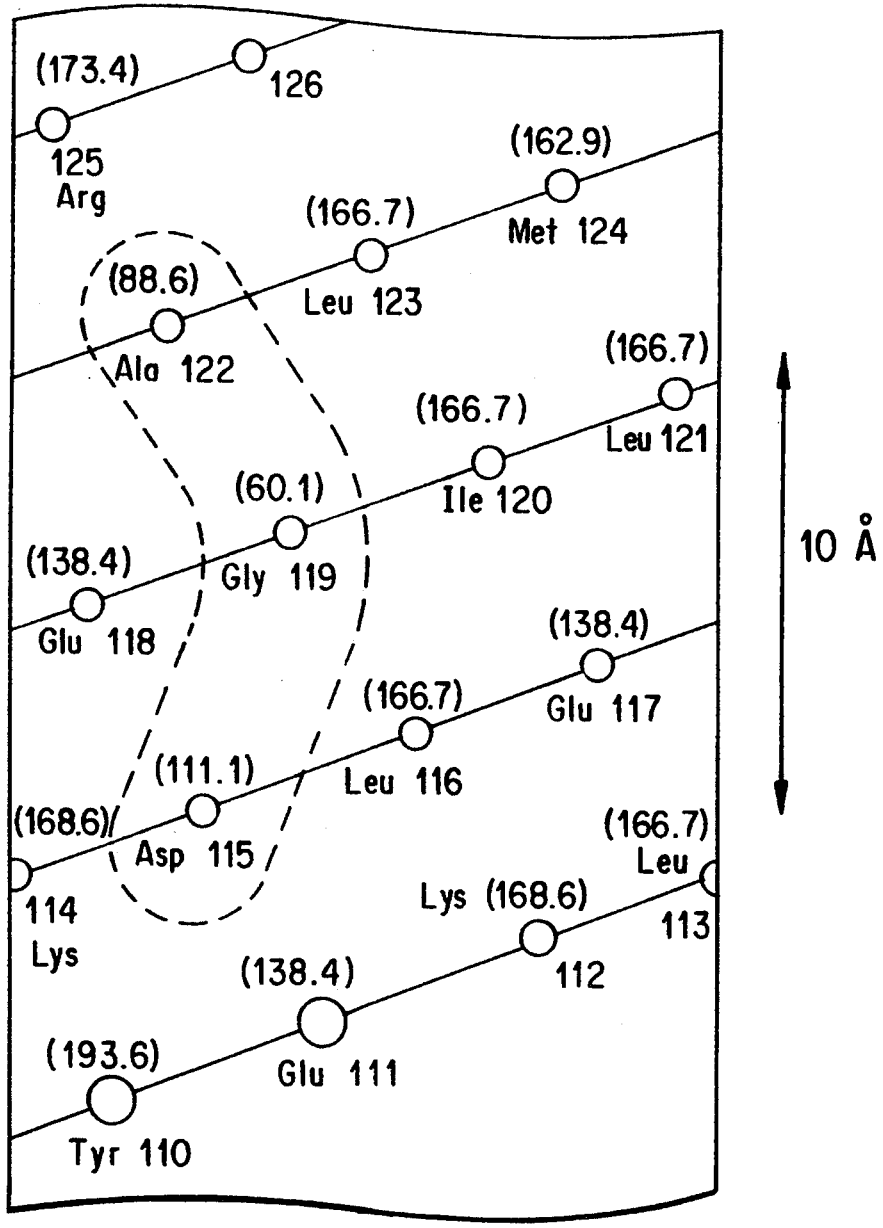
FIG. 3 is an idealized surface net (cylindrical plot) representation of most of the third alpha helix of bovine growth hormone. The surface net is produced by projection of the helix onto a coaxial cylindrical sheet of paper, cutting this paper parallel to the helical axis and flattening it. The volumes of the amino acids are given in parentheses. A dashed line indicates the cleft or depression formed by Ala122-Gly119-Asp115.
Figure 4:
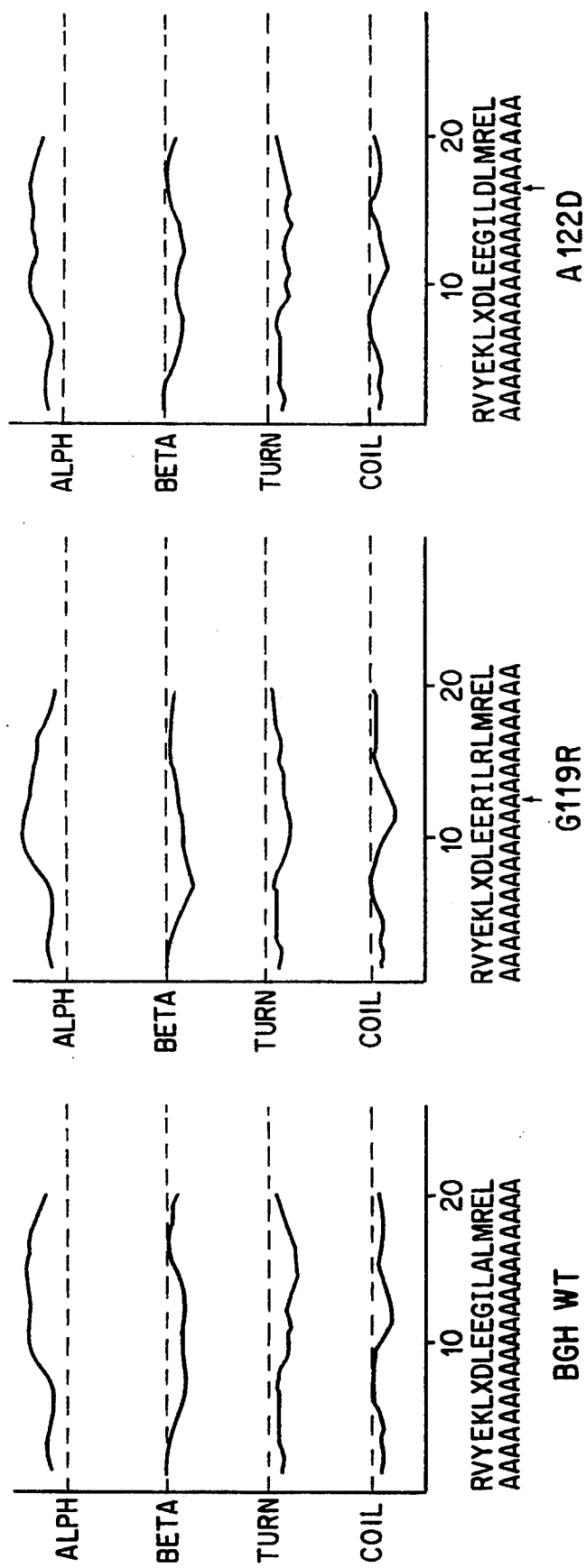
FIGS. 4a–4c are a plot of the secondary structure prediction (alpha-helix, beta-sheet, reverse turn, random coil) for amino acids 108–127 of bovine growth hormone (a) wild-type (b) the mutant G119R and (c) the mutant A122D. These plots were generated by the "Micro-Genie" program.

The amino acid sequence of the growth hormones isolated from various vertebrate species are highly conserved. In a comparison of flounder growth hormone with other growth hormones, including bGH, Watahiki, et al., J. Biol. Chem., 264:312 (1989) identified five conserved regions. Watahiki's conserved region GD4 comprises the stretch LKDLEEGILALM-RELED of bovine growth hormone, i.e.,residues 113 to 129. Watahiki's FIG. 3 identifies residues conserved among the GHs and residues predicted to be important for the manifestation of growth-promoting activity.

Studying Watahiki's GD4 consensus region, several families of growth hormones may be discerned. The first family (I) comprises cGH, rGH, pGH oGH, bGH, and hGH. These begin with LKDLEEGI. They then continue with IQA (cGH, rGH, pGH), ILA (oGH, bGH) or IQT (hGH). All members of family I then conclude GD4 with LMRELED (except for rGH, LMQELED. and hGH, LMGRLED). The second family (II) comprises fGH, yGH, tGH and sGH. These have the consensus sequence LS (E/D) LK (M/T) G(L/I) (L/G/H/N) (K/L) LI (E/T/R/I) (A/G) (N/S) QD.

Four amino acids in GD4 are conserved among all of the growth hormones noted by Watahiki: Leu 113, Leu 116, Gly 119, Leu 123 and Asp 12 (numbering according to the bGH sequence). Of the amino acids nearest Gly 119 on the face of the third alpha helix, Asp115 is strongly conserved (replaced by Glu in the fish hormones); Leu 116 is invariant, Glu 118 is conserved among the mammals and birds, but replaced by Met, Thr or Val in fish; Ile 120 is almost invariant (replaced by Leu in fGH), and Ala 122 is well conserved, especially in mammals and birds (replaced by Thr in hGH and Leu or Lys in fish GHs). (It should be understood that the present invention is not limited to mutants in which these conservations are maintained.)

It has been shown that a recombinant molecule containing a hGH-(1-134) fragment linked to a human placental lactogen-(141-191) fragment retained full hGH immunological activity and binding affinity to GH receptors isolated from rabbit liver. Russell, et al., J. Biol. Chem., 256: 296-300 (1981). By using the homolog-scanning mutagenesis technique, gene fragments of homologous hormones—i.e., human placental lactogen or human prolactin—were systematically substituted throughout the hGH gene, thus producing various chimeric hormones. Cunningham, et al., Science, 243:1330-36 (1989). A comparison of the binding affinities of these mutants GHs and wild-type hGH to a cloned liver hGH receptor led to the conclusion that there were three discontinuous polypeptide determinants in hGH involved in receptor binding. They were located at the $NH_2$ terminus, COOH terminus, and within a loop between amino acid residues 54 and 74. These putative binding domains were further analyzed by an alanine-scanning mutagenesis technique in which alanine residues were systematically substituted throughout those regions. Amino acid residues at positions 10, 58, 64, 68, 172, 174, 175 and 176 of hGH were shown to be important for GH receptor binding. However, non of the mutant GHs were reported to inhibit growth. Cunningham, et al., Science, 244:1081-85 (1989).

The present invention is not limited to the mutation of the third alpha helix of bovine or human growth hormone. Rather, it encompasses the mutation of the third alpha helix of any mammalian or other vertebrate growth hormone, including, but not limited to, the growth hormones whose sequences are given in Watahiki (1989): flounder, yellowtail, tuna, salmon, chicken, rat, porcine, ovine, bovine and human growth hormones. Expression of mutants of other growth hormones is facilitated by the availability of genes encoding the latter. See, e.g., Goeddel, Nature, 281:544-548 (1979) (hGH).

The concept of polypeptide which is substantially homologous to bovine growth hormone is deeded to include (but is not limited to) any polypeptide which differs from bovine or human growth hormone by (a) a substitution at an amino acid corresponding to amino acids 115 or 119 of bovine growth hormone, (b) a substitution at an amino acid corresponding to an amino acid of bovine or human growth hormone which is not conserved among the vertebrate growth hormones, especially the replacement of that amino acid by one found at the site in a different growth hormone, and/or (c) truncation of amino acids 1-95 and/or 134-191. (conserved amino acids are identified in Watahiki, et al., 1979.) Thus, all non-bovine vertebrate growth hormones are "substantially homologous" with bovine and/or human growth hormone. Preferably, the polypeptide is at least about 50% homologous, more preferably at least 80% homologous, with bovine or human growth in the subsequence substantially corresponding to the third alpha helix (approximately, residues 106-129) of bGH, and more preferably over the entire length of the polypeptide (ignoring extraneous non-bGH-related fusions to the amino- or carboxy-terminal).

The compound is considered to be growth-inhibitory if the growth of test animals of at least one vertebrate species which are treated with the compound (or which have been genetically engineered to express it themselves) is significantly (at a 0.95 confidence level) slower than the growth of control animals (the term "significant" being used in its statistical sense). Preferably, it is growth-inhibitory in a plurality of species, or at least in humans and/or bovines. Growth hormones have considerable interspecies cross-reactivity. Gill, et al., Biotechnology, 3:643 (1985) reported that recombinant chicken and bovine growth hormones accelerate growth in juvenile pacific salmon.

It is known that certain fragments or growth hormones also have growth-promoting activity, and it is expected that the growth-inhibitory peptides (the term is used hereafter to include proteins) of the present invention need not be as large as bGH. Preferably, the peptides are at least 11 amino acids long (three turns of an alpha helix) and more preferably at least 50 amino acids long. These peptides may retain the growth inhibiting action of, e.g., bGH (G119R), yet lack other, undesirable biological activities of the native size mutant. They may also have more desirable pharmacokinetic characteristics.

The growth inhibitory peptides of the present invention may also be largen than bGH, provided that the additional amino acids do not result in the compound being unable to reduce the growth rate of a vertebrate.

While the mechanism of action of applicant's growth inhibitory peptides is not known, it is believed that they function as antagonists to wild-type growth hormones endogenously produced by the target animal. We have shown that, e.g., bGH (G119R) and bGH (G119r, E117L, A122D), both competitively inhibit the binding of wild type bGH to liver membrane preparations. Thus, it is believed that the compound has a net result of inhibiting growth because its growth-promoting activity is substantially less than that of wild type growth hormones (and perhaps is negligible) yet it can displace from growth hormone receptor (GHR) sites the endogenous native growth hormone (whose stimulation of growth would have been more pronounced). However, applicants are not bound by this theory.

Figure 5:
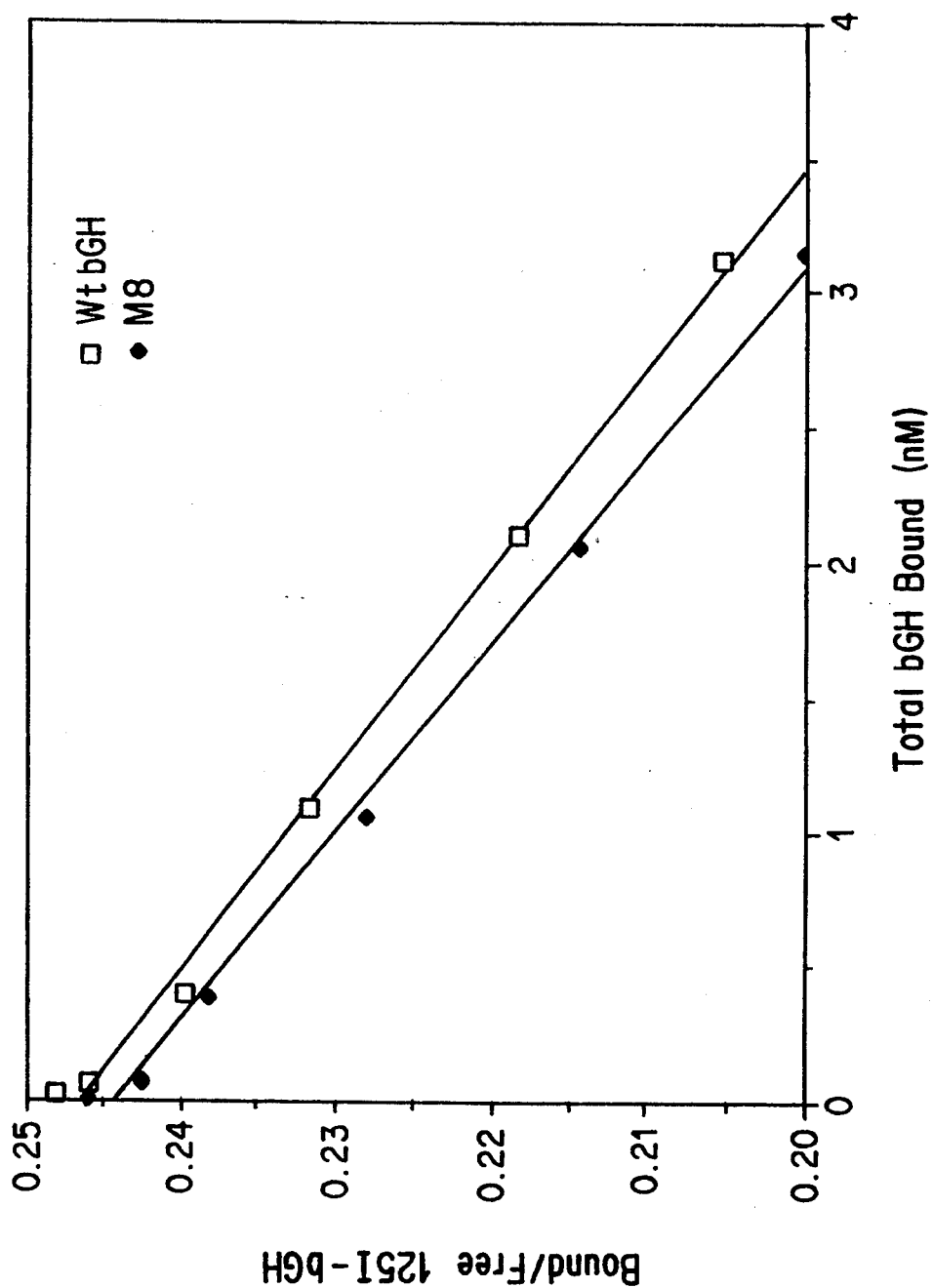
FIG. 5 Scatchard plots of data from competitive binding experiments for wild type bGH and bGH-M8 using mouse liver membrane preparations. The ordinate represents the ratio of bound to free bGH and the abscissa the concentration of total bGH bound. Each point represents the mean of four experiments which were carried out in triplicate.
Figure 6:
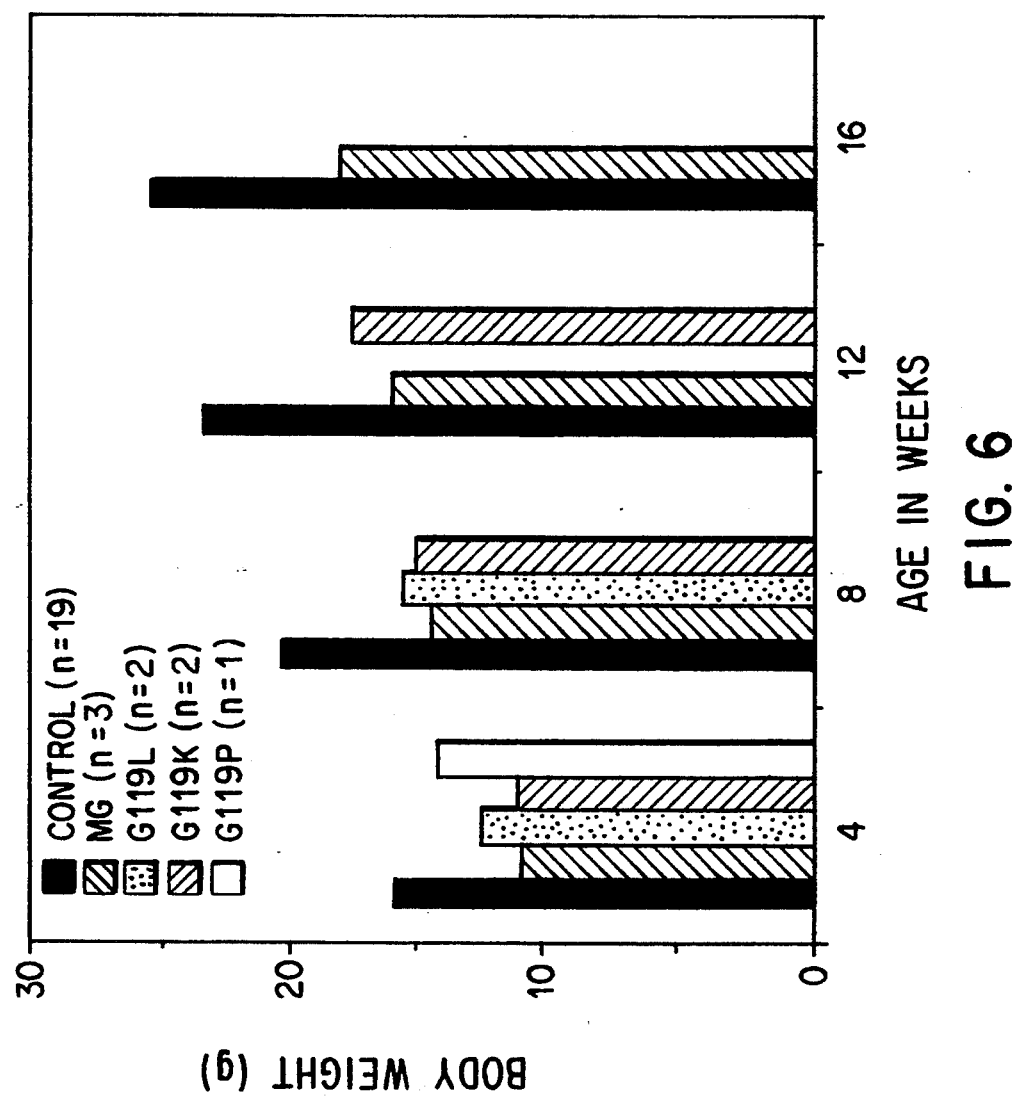
FIG. 6 provides a growth rate comparison among control (non-transgenic), G119R, G119L, G119K and G119P mice, illustrating the growth-inhibitory effect of these mutants.
Figure 7:
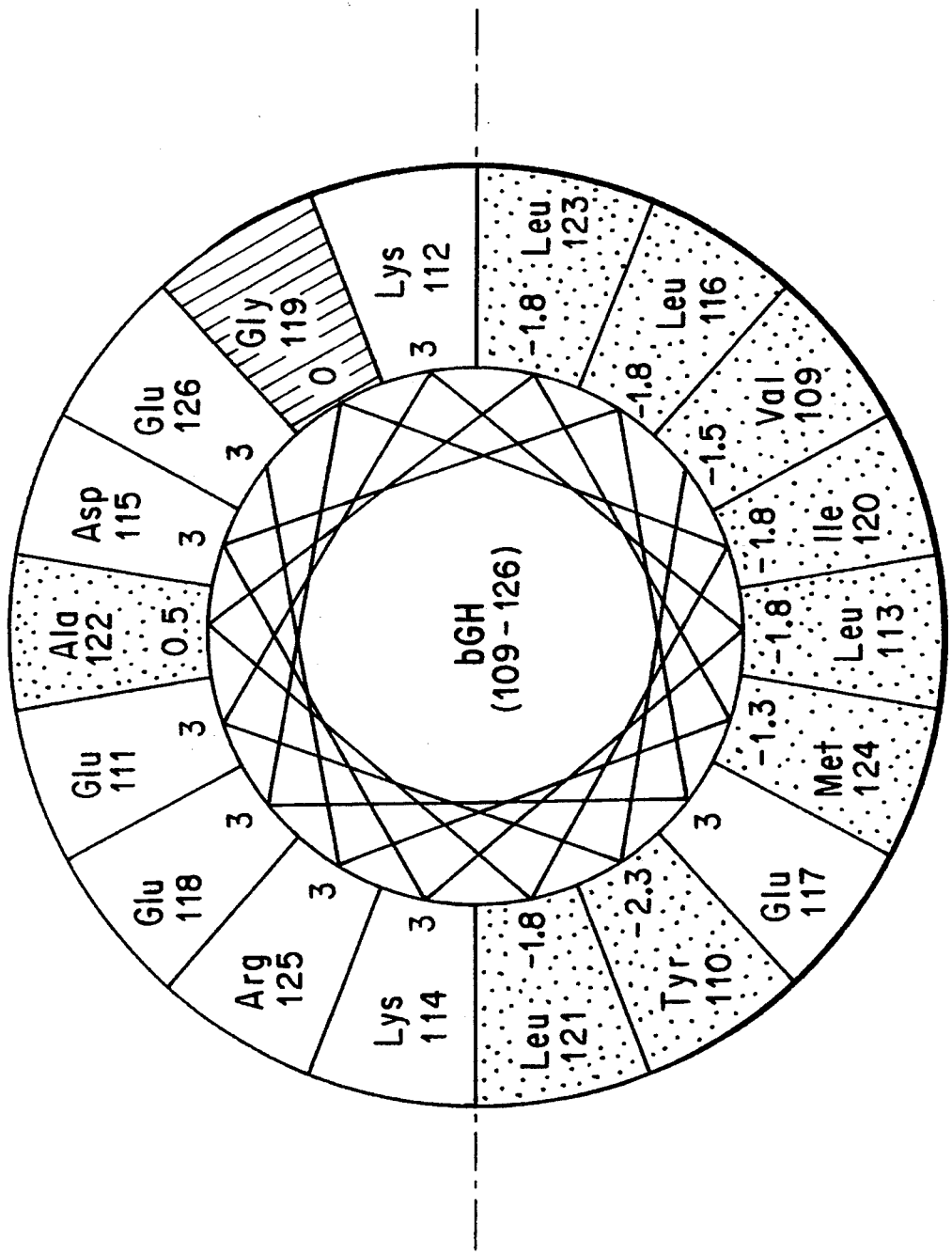
FIG. 7 presents an axial view of the third alpha helix (109–126) of bGH, showing its amphipathic tendencies.

DeVos, et al., Science, 255:306 (1992) examined the complex of hGH and the extracellular domain of its receptor (hGHR) by X-ray diffraction. The first receptor-binding region of hGH is concave and is formed mainly by residues on exposed faces of helix 4, but also by exposed residues of helix 1 and residues in the region connecting helices 1 and 2. The second receptor-binding region comprises the exposed sides of helices 1 and 3 and is relatively flat. The role of the helix 3 is shown best in DeVos' FIG. 5; there is a significant decrease in solvent accessibility around hGH E119 upon complex formation. The complex had the form hGH $(hGHR)_2$;

that is, the receptor dimerizes to interact with hGH. It is possible that our GH antagonists interfere with this dimerization.

Preferably, the compounds of the present invention have an ED50 which is less than about 10 times the ED50 of wild type bGH in an assay of the ability of the compound to displace radiolabeled wild type bGH from a liver membrane preparation made as described below. More preferably, the compounds have an ED50 at least comparable to that of wild type bGH. Most preferably, the compounds have a higher affinity for growth hormone receptors than does the growth hormone native to the animal receiving the compound. For purification and characterization of a human growth hormone receptor, see Leung, et al., Nature, 330:537–43 (1987).

A GH mutein may be considered an antagonist, even if it lacks growth-inhibitory activity, if it antagonizes another GH-mediated activity, e.g., its diabetogenic, glomerulosclerotic, hypercholesterolemic, or tumorigenic activities.

The preferred growth-inhibitory peptides are characterized by a modification of the surface topography of the third alpha helix. It will be seen from FIG. 3 that in the third alpha helix of "wild-type" bovine growth hormone, there is a surface cleft or depression beginning, at the Aspartate-115, deepening at the Glycine-119, and ending with the Alanine-122. All of the mutants prepared so far, both those which retain the wild-type growth-promoting activity and those which do not, are consistent with the theory that growth-promoting activity requires the presence of this cleft or depression and that, if the center of this cleft is "filled in" by substitution of amino acids with bulkier side chains, the mutein inhibits the growth of the subject.

Mutations which substantially destabilize the alpha-helix are undesirable since they may result in the loss of all growth-related activity. We have observed such loss in the case of several mutations which were expected to disrupt the alpha helix.

For a discussion of alpha helix formers and breakers, see Chou and Fasman, supra. Glu, Ala and Leu are the preferred alpha helix formers while Pro and Gly are characterized as strong helix breakers. Substitutions which introduce strong alpha helix breakers are less desirable, but may be tolerated in a particular case, such as the end of the helix. The secondary structures of our analogues have been predicted using the "Micro Genie" computer program, which uses the algorithm of Garnier, et al., J. Biol. Chem., 120:97–120 (1978).

With respect to amino acid 119, glycine is both the smallest amino acid residue and the one least favorable to alpha-helix formation. Thus, it is believed that any other amino acid may be substituted for it without destabilizing the alpha helix, while at the same time filling in the aforementioned cleft. All of the $G^{119}$ bGh substitutions tested resulted in a "small animal" phenotype. These substitutions were arginine (a large, positively charged AA), proline (a cyclic aliphatic AA), lysine (a large, positively charged AA), tryptophan (a large aromatic AA) and leucine (a large, nonpolar, aliphatic AA). In hGH, the homologous glycine is at position 120. Substitution of arginine or tryptophan resulted in an antagonist, however, hGH G120A retained growth-promoting activity. Consequently, it is presently believed that this glycine, which is conserved in all vertebrate GHs, may be replaced by any amino acid other than alanine (the second smallest amino acid), and more preferably by any amino acid which is at least as large as proline (the smallest replacement amino acid known to result in a "small" animal phenotype). The deletion of $G^{119}$ is also known to result in a "small" animal phenotype.

Modification of position 115 is suggested by our "cleft" theory. The aspartate at position 115 may be replaced by a bulkier amino acid which does not destroy the alpha helix. Preferably, the replacement amino acid has a size greater than that of aspartate. The amino acids histidine, methionine, isoleucine, leucine, lysine, arginine, phenylalanine, tyrosine and tryptophan are substantially larger than aspartate. Of these, His, Met, Leu and Trp are more preferred because they combine the advantages of bulk with a reasonably strong alphahelical propensity. Note, however, that the Glu is the strongest alpha-helix former of all of the amino acids. The D115A mutant of bGH is not a GH antagonist, but Alanine is smaller than Aspartic Acid, so this is not probative of the value of replacing Asp;115 with a bulkier amino acid.

It is possible that G119A might lead to a "small" phenotype if coupled with other mutations, e.g., at 115 and 122.

It is possible to systematically screen for the effect of all possible amino acid substitutions at positions 115 and 119. (There are $20^2 - 1$ or 399 combinatorial possibilities.) DNA which encodes bGH and is degenerate at these positions, so as to there encode all possible amino acids, or only those with acceptable alpha-helical propensities, is prepared, e.g., by a "dirty bottle" synthesis. Phage are prepared, as taught by Ladner, et al., PCT/US89/03731, W090/02809, which display the mutant bGHs as a domain of a chimeric coat protein. The phage are incubated with a chromatographic support bearing a growth hormone receptor. (For the techniques of isolating growth hormone receptors, see Leung, et al., Nature 330:537 (1987) and Spencer, et al., J. Biol. Chem., 263:7862 (1988)). Native bGH is also incubated with the support, before, during or after the phage incubation. Bound phage are recovered, amplified and examined to determine the sequence of the mutant bGH (usually by sequencing the corresponding gene in the phage genome). These mutants have demonstrated the ability to compete with wild type bGH for a growth hormone receptor. Their ability to antagonize GH activity in vivo is then confirmed by, e.g., administering them directly to an animal or by preparing a suitable transgenic animal, or by the in vitro assay described in Example 7. This approach may be extended, if desired, to other amino acid positions in the third alpha helix. Amino acids which are particularly preferred for screening are the six amino acids spatially nearest bGH's Gly119, that is, Ala122, Leu123, Ile120, Leu116, Asp115 and Glu118. It should be noted that Bass, et al., Proteins: Structure, Function and Genetics, 8:309–314 (1990), prepared "hormonephage" which express and displayh GH-geneIII fusion proteins and which were bound by anti-hGH monoclonal antibodies. Moreover, it was possible to separate phage bearing Wt-hGH from phage bearing the low affinity hGH mutant R64A by means of affinity chromatography (using the extracellular domain of the hGH receptor bound to nonporous oxirane beads).

Besides the mutations at position 119, which is deemed necessary to impart the desired growth-inhibitory activity, additional mutations are possible which will leave the growth-inhibitory activity or other antagonist activity intact. These mutations may take the form of single or multiple substitutions, deletions, or insertions, in nonessential regions of the polypeptide. For example, it is possible to alter another amino acid in the alpha helix provided that the substitution does not destroy the alpha helix. Preferably, such alterations replace an amino acid with one of similar size and polarity. It may be advantageous to modify amino acids flanking the primary mutation site 119 in order to increase the alpha-helical propensities of the sequence, particularly if the mutation at 119 is one expected to destabilize the helix.

The following table may be helpful in identifying candidate mutants:

| AA | Volume (angstroms) | Alpha Helicity |
|---|---|---|
| Gly(G) | 60.1 | 0.53 |
| Ala(A) | 88.6 | 1.45 |
| Ser(S) | 89.0 | 0.79 |
| Cys(C) | 108.5 | 0.77 |
| Asp(D) | 111.1 | 0.98 |
| Thr(T) | 116.1 | 0.82 |
| Asn(N) | 117.7 | 0.73 |
| Pro(p) | 122.7 | 0.59 |
| Glu(E) | 138.4 | 1.53 |
| Val(V) | 140.0 | 1.14 |
| Gln(Q) | 143.9 | 1.17 |
| His(H) | 153.2 | 1.24 |
| Met(M) | 162.9 | 1.20 |
| Ile(I) | 166.7 | 1.00 |
| Leu(L) | 166.7 | 1.34 |
| Lys(K) | 168.6 | 1.07 |
| Arg(R) | 173.4 | 0.79 |
| Phe(F) | 189.9 | 1.12 |
| Tyr(Y) | 193.6 | 0.61 |
| Trp(W) | 227.8 | 1.14 |

Several of the cited references provide guidance as to where and where not the polypeptide will tolerate mutagenesis. Watahiki, et al. (1989) compared the sequences of flounder, yellowtail, tuna, salmon, chicken, rat, porcine, ovine, bovine and human growth hormones. He identified five conserved domains which he labeled GD1–GD5. Mutations in these conserved domains are more likely to affect activity; GD4 corresponds to the third alpha helix of bGH. In mutating a known GH antagonist with the desire to retain inhibitory activity, mutations outside the conserved domains are more prudent. However, mutations in these conserved regions, if carefully chosen, may be tolerated; for example, the mutation E117L does not modify the activity of either wild-type bGH or a bGH G119R mutant. Note that not only substitutions, but also insertions and deletions, are suggested by the example of the cognate hormones.

Abdel-Meguid, et al. (1987) determined the 3D-structure of recombinant methionyl porcine growth hormone, and suggested that it revealed the "general three dimensional fold" of the growth hormones. The 3D-structure can be used to identify interior and surface residues; generally speaking, proteins mutated at surface residues (other than the receptor binding site) are more likely to remain functional. However, Creighton and Chothia, Nature, 339:14 (1989) discuss the toleration of mutations at buried residues. The structure may also be used to determine flexible surface "loops"; proteins are more tolerant of deletions and insertions in such regions.

Cunningham, et al. (1989) used homolog-scanning mutagenesis to identify the epitopes of hGH for its cloned liver receptor. Only variant hormones having mutations in regions C(54–74), F(164–190), and, to a lesser extent, A(11–33) exhibited reduced binding affinity. Cunningham and Wells, Science, 244:1081 (1989) used a related technique, alanine-scanning mutagenesis, to further study these regions. Note, however, that binding to the receptor utilized by Cunningham is not necessarily critical to the growth-promoting or growth-inhibitory activity of the mutant.

For example, it seems likely that major amino- and carboxy-terminal truncations can be made without adverse effects on growth-inhibitory activity, since the 96–133 fragment of bGH (K112L) is understood to retain bioactivity. Truncations may be generated by gene modification or by exopeptidase treatment.

In terms of the kinds of substitutions which may be made, one may look first to analyses of the frequencies of amino acid changes between homologous proteins of different organisms, such as those presented in Table 1-2 of Schulz and Schimer, supra and FIGS. 3–9 of Creighton, supra. Based on such analyses, we define conservative substitutions as exchanges within the groups set forth below:

I—small aliphatic, nonpolar or slightly polar residues—Ala, Ser, Thr (Pro, Gly)

II—negatively charged residues and their amides Asn Asp Glu Gln

III—positively charged residues—His Arg Lys

IV—large aliphatic nonpolar residues—Met Leu Ile Val (Cys)

V—large aromatic residues—Phe Tyr Trp

Three residues are parenthesized because of their special roles in protein architecture. Gly is the only residue without a side chain and therefore imparts flexibility to the chain. Pro has an unusual geometry which tightly constrains the chain. Cys can participate in disulfide bonds which hold proteins into a particular folding; the four cycteines of bGH are highly conserved. Note that Schulz and Schimer would merge I and II above. Note also that Try, because of its hydrogen bonding potential, has some kinship with Ser, Thr, etc.

Within the growth hormone family itself, we see a wide variety of substitutions of other amino acids for the residues of bGH. For example, among the vertebrate GHs set forth in Watahiki, et al., (1989), Pro appears 6 times in bGH. The first Pro is not substituted, but is absent from sGH. The second is replaced by Leu in fGH; Thr in yGH and tGH, Val in sGH. The fourth Pro is conserved. The fifth Pro is replaced by Phe in fGH; Ser in yGH. The sixth Pro is replaced by Phe in fGH, yGH and tGH, and Leu in sGH. Overall, Pro is replaced 4 times by Phe, 3 times by Leu, 2 times each by Thr and Ile, and once each by Val and Ser. When this analysis is extended to all amino acids of bGH, we obtain the following tallies:

Ala (14; 2 conserved)——>
Thr (14), Ser (11), Asp (7), Ile (4), Glu (4), Gly (4), Val (3), Gln (3), Leu (3), Lys (2), Phe (1), Asn (1)]

Asp (10; 2 conserved)——>
Tyr (6), Asn (4), Val (4), Glu (3), Lys (2), Arg (2), Gly (2), Thr (1), Ser (1), Phe (1), Ala (1)

-continued

Glu (13; 2 conserved)——→
    Asp (14), Lys (10), Gln (4), Ala (3), Pro (2), Thr (2), Asn (1), Ser (1), Val (1), Met (1), Arg (1), Gly (1)

Phe (13; 3 conserved)——→
    Tyr (7), Leu (6), Asn (6), Ser (5), Gln (3), Ile (2), Gly (2), His (1), Thr (1), Val (1)

Gly (10; 1 conserved)——→
    Arg (9), Glu (8), Asp (7), Val (4), Pro (4), Ser (4), Asn (3), Phe (3), Asp (2), His (1), Thr (1), Tyr (1), Ala (1)

His (3; 1 conserved)——→
    Arg (1), Asn (1), Tyr (1), Asp (1)

Ile (7)——→
    Gln (7), Asn (5), Leu (4), Phe (4), Val (4), Ala (2), Ser (1), Arg (1)

Lys (12; 2 conserved)——→
    Ser (11), Arg (7), Gly (4), Gln (2), Leu (2), Asn (1)

Leu (27; 11 conserved)——→
    Ser (11), Val (9), Asn (7), Met (7), Gln (7), Arg (4), Glu (4), Phe (3), Tyr (3), Gly (1), Pro (1), His (1)

Met (4)——→
    Ile (7), Ala (4), Thr (3), Ser (3), Leu (1), Asn (1), Val (1)

Asn (6)——→
    Ile (8), His (4), Asp (3), Gln (3), Glu (2), Ser (1)

Pro (6; 1 conserved)——→
    Phe (4), Leu (3), Thr (2), Ile (2), Val (1), Ser (1)

Gln (11; 1 conserved)——→
    Leu (13), Arg (6), Lys (5), Ser (4), Glu (4), His (1), Gly (1), Asp (1), Pro (1)

Arg (13; 1 conserved)——→
    Lys (11), Ser (9), Thr (7), Ile (3), Glu (2), Gly (2), Asn (2), His (2), Val (1), Gln (1), Asp (1), Ala (1)

Ser (13; 3 conserved)——→
    Ala (8), Asn (8), Gln (4), Leu (4), Gly (3), Glu (2), Asp (2), Thr (2), Arg (1), Val (1)

Thr (12; 1 conserved)——→
    Ser (14), Ala (13), Val (7), Tyr (5), Phe (4), Ile (4), Met (3), Leu (3), Pro (2), Asn (2), Gly (1)

Val (6)——→
    Ala (4), Ser (4), Ile (3), Thr (2), Gln (6), Gly (2), Met (2), Leu (1), Lys (1)

Tyr (6)——→
    Leu (5), Pro (4), Gln (3), Phe (2), Glu (1), Ser (1)

Note that the above figures are not normalized to adjust for the relative frequencies of occurrence of the various amino acids. We further note that in our own mutagenesis experiments, changing Lys 112 to Leu or Lys 114 to Trp (M1), Glu to Gly (E126G) or Leu (M4), or Ala to Thr (A122T) did not alter activity, while changing Lys, Glu or Leu to Pro abolished activity.

The present invention is not limited to any particular method of producing the desired GH antagonists. Preferably, these antagonists are produced by first altering a gene encoding a vertebrate GH (e.g., bGH or hGH) having the "native" third alpha helix by site-specific mutagenesis, and then cloning and expressing the altered gene in a suitable host. Molecular biology techniques are described in, e.g., Sambrook, et al., *Molecular Cloning: A Laboratory Manual* (Cold Spring Harbor Lab Press; 2nd ed., 1989). The gene may be of genomic origin, it may be cDNA prepared from bGH messenger RNA, it may be synthetic, or it may be a combination thereof. For the amino acid sequence of bGH and for the cDNA sequence of the bGH gene, see Miller, et al., J. Biol. Chem., 255:7521-24 (1980). For the genomic bGH sequence, see Woychick, et al., Nucleic Acids Res., 10:7197-7210 (1982). The cDNA sequence for hGH is given by Chang, et al., Gene, 55:189 (1987) and DeNoto, et al., Nucleic Acid Res. 9:3719 (1981), and the genomic hGH sequence is in Robbins, et al., Cell, 29:623 (1982).

The host may be any convenient organism, including a bacterial, yeast, or mammalian cell. The gene is operably linked to a promoter functional in the host. A constitutive promoter would activate gene expression in a general manner, i.e., in many tissue and at all times during development. A regulatable promoter may be activated in a tissue or cell specific manner, at precise time during development, or in response to changes in the environment. A constitutive promoter is usually employed when larger amounts of gene product (usually protein) is required or when the gene product is required in many cells of many tissues. A regulatable promoter is utilized when one gene product is required in a small number of cells of a particular tissue or at a given time during development.

The expression system may be engineered so that the antagonist is secreted into the culture medium, or the host cells may be grown to a high cell density and they lysed to release the compound.

One method suitable for the purification of bGH (G119R) and the like is described in Leung, et al., Endocrinology, 119:1489-1496 (1986). Essentially, this procedure involves purification by (a) ammonium sulfate precipitation, (b) fractionation on DEAE-cellulose (or any equivalent ion-exchange column), and (c) gel filtration (e.g., on a Sephadex G-25 and/or Sephacryl S-200 column). Other procedures applicable to purification of growth hormone-related compounds are set forth in Reichert, Jr., "Purification of Anterior Pituitary Hormones: Bovine, Rat and Rabbit, " Meth. Enzymol., 37:360 et seq. (Academic Press, N.Y.:1975). Polyclonal or monoclonal antibodies which specifically recognize the protein of interest may also be used in the purification process.

The purified antagonist may then be combined with compatible, nontoxic pharmaceutical excipients and administered to an animal, e.g. to treat a condition characterized by an excessive growth rate. (The term "animal" is intended to include humans.) In the case of administration to nonhuman animals, it may be preferable to incorporate the drug into the animal's feed, possibly in a prepared combination of drug and nutritional material ready for use by the farmer. The antagonist may be administered orally or parenterally (including intravenously, subcutaneously and intramuscularly) to humans, in any suitable pharmaceutical dosage form. In the case of treatment of retinopathy, it may be administered directly to the eye by means of a conventional ocular pharmaceutical form. An effective dosage and treatment protocol may be determined by conventional means, starting with a low dose in laboratory animals and then increasing the dosage while monitoring the effects, and systematically varying the dosage regimen as well. The trial dosages would be chosen after consideration of the clinical literature with respect to administration of growth hormones, and of somatostatin (a growth hormone release inhibitor).

In another embodiment, the gene is introduced into a host cell which is developed into genetically transformed cells of a transgenic animal. Linearized DNA bearing the growth hormone antagonist gene may be introduced into a gamete, or microinjected into the pronuclei of fertilized eggs, into the cytoplasm, into the nuclei of two-cell embryos, into individual cells of a blastocyst, or into the blastocoel cavity. (Some of these targets may be reached by electroporation instead of microinjection.) Alternatively, a retrovirus bearing the gene may be constructed and used to infect preimplantation embryos or tissue culture cells (e.g., embryonic stem cells) which may be aggregated with such embryos. In either case, the genetically modified zygote, after a brief in vitro cultivation, is implanted into a foster mother and carried to term. For "gene therapy" post partum, see Cline, et al., Nature, 284:422–425 (1980); Williamson, Nature, 298:416–18 (1982). Again, the gene is operably linked to a promoter functional in the host, and the promoter may be constitutive or regulatable. Preferably, expression is regulated so abnormal embryonic or fetal development is avoided.

The invention is further illustrated, without limitation, by the following examples.

EXAMPLE 1

Generation of Mutations Conferring the Reduced Growth Phenotype

Materials and Methods

The plasmid, pBGH-1Odelta6, was derived from pBGH-1O and contains the complete coding region of bGH and intron A. Bovine growth hormone introns B, C and D are absent (FIG. 1). This plasmid encodes "wild type" bGH, and its expression is controlled by a 1700 base pair segment of the mouse metallothionein I transcriptional regulatory sequence.

Plasmids pBGH-1Odelta6-$G^{119}R$ and pBGH-1Odelta6-$E^{117}L$, $G^{119}R$, $A^{122}D$ were derived from pBGH-1Odelta6 and were generated by segment-directed mutagenesis using complementary oligonucleotides to replace the DNA between the Tth111I site (found near the 3' end of Exon IV) and the Xma I site (located near the 5' end of Exon (V). The other mutations described herein were generated similarly.

The complementary oligonucleotides used for pBGH1O delta 6-$G:^{119}R$ were: 5'GTGTCTAT-GAGAAGCTGAAGGACCTGGAGGAAAG-GAATCCTGGCCTGATGCGGGAGCTGGA AGATGGCACCCC 3'; 73-MER) and (5'CCGGGGGGTGCCATCTTCCAGCTCCC-GCAT CAGGGCCAGGATCCTTTCCT-CCAGGTCCTTCAGCTTCTCATAGAC 3'; 76-MER).

The complementary oligonucleotides used for pBGH1Odelta6-$E^{117}L$, $G^{119}R$, $A^{122}D$ were: (5'GTGTCTATGAGAAGCTGAAGGACCTGCT-GGAAAGGATCCTGGACCTGATGCG-GGAGCTG GAAGATGGCACCCC 3'; 73-mer) and 5' CCGGGGGGTGCCATCTTCCAGCTCCCGC ATCCAGGTCCAGGATCCTTTCCAG-CAGGTCCTTCAGCTTCTCATAGACA 76-mer). These oligonucleotides hybridize as follow:

```
G119R
 GT GTC TAT GAG AAG CTG AAG GAC CTG GAG GAA AGG ATC CTG GCC
 ACA CAG ATA CTC TTC GAC TTC CTG GAC CTC CTT TCC TAG GAC CGG
 Arg Val Tyr Glu Lys Leu Lys Asp Leu Glu Glu Arg Ile Leu Ala

CTG ATG CGG GAG CTG GAA GAT GGC ACC CC
 GAC TAC GCC CTC GAC CTT CTA CCG TGG GGG GCC
 Leu Met Arg Glu Leu

E117L, G119R, A122D
 GT GTC TAT GAG AAG CTG AAG GAC CTG CTG GAA AGG ATC CTG GAC
 ACA CAG ATA CTC TTC GAC TTC CTG GAC GTC CTT TCC TAG GAC CGG
 Arg Val Tyr Glu Lys Leu Lys Asp Leu Leu Glu Arg Ile Leu Asp

CTG ATG CGG GAG CTG GAA GAT GGC ACC CC
 GAC TAC GCC CTC GAC CTT CTA CCG TGG GGG GCC
 Leu Met Arg Glu Leu
```

These oligonucleotides encode DNA changes which result in the substitutions of arginine for glycine at position 119 in pBGH-1Odelta6-G119R; and leucine for glutamate at position 117, arginine for glycine at position 119 and aspartate for alanine at position 122 in pBGH-1Odelta6-$E^{117}L$, $G^{119}R$, and $A^{122}D$. These amino acids were chosen because they have hydrophilic (arginine and aspartic acid) or hydrophobic (leucine) character [See Hopp and Woods, PNAS (USA), 78:3824–28 (1981)], positively (arginine) or negatively (aspartic acid) charged side chains [See Kaiser and Kezdy, Science acid) 223:249–55 (1984)], and high α-helical-forming potential [See Chou and Fasman, Ann.

Rev. Biochem., 47:251-76 (1978)] furthering generation of an idealized amphiphilic α-helix [See Margalit, et al., J. Immunol., 138:2213-29 (1987); Brems, et al., Biochemistry 26:7774-78 (1987); Kaiser and Kezdy, supra; Chen, et al., PNAS (USA), 87:5061-65 (July 1990]. In addition, these oligonucleotide duplexes encode a silent base-pair change designed to create a unique BamHI restriction site which simplified screening procedures. The oligonucleotides were annealed and subcloned between the TthlllI and XmaI sites using standard procedures (Maniatis et al., Molecular Cloning (Cold Spring Harbor: (1982)). Mutant plasmid DNA's were identified by digestion with BamHI restriction site which simplified screening procedures. The oligonucleotides were annealed and subcloned between the TthlllI and XmaI sites using standard procedures (Maniatis et al., Molecular Cloning (Cold Spring Harbor: 1982). Mutant plasmid DNA's were identified by digestion with BamHI.

The nucleotide sequence of the mutated bovine growth hormone target regions were determined by using the dideoxy chain-termination method with modified T7 DNA polymerase (Sequenase, United States Biochemical; Sanger et al., PNAS (USA), 74:5463-67 (1977)). Oligonucleotide primers for manual DNA sequencing were synthesized using the DuPont Coder #300 DNA synthesizer and purified by denaturing polyacrylamide gel electrophoresis, passive elution and concentration by ethanol precipitation. The oligonucleotide primers used for the direct sequencing analysis of the two mutants was the following: 18mer (5'AAATTTGTCATAGGTCTG 3'). Briefly, 1—3 μg of doublestranded plasmid DNA was denatured in the presence of 0.2N NaOH, and 10–20 pmoles of oligonucleotide primer was allowed to anneal (65° C., 2 min. followed by 30 min. slow cool) to the denatured template. A two-step polymerization was performed by using the modified T7 DNA polymerase which extends the oligonucleotide-primed chain in the presence of dNTP's and deoxyadenosine triotriphosphate (>1000 Ci/mmole, Amersham) followed by transfer of equal aliquots into each of four specific dideoxynucleotide mixes which randomly terminate chain elongation. Following addition of a formamide termination buffer to each reaction, the samples were incubated at 80° C. for 2 min. and the DNA sequence was determined after size fractionation of the four sets of fragments by 10% polyacrylamide/8M urea electrophoresis and autoradiography.

EXAMPLE 2

Expression in Mammalian Cells in Culture

Using the in vitro mutagenesis protocols described above, two mutant bGH genes were generated initially: one converts glycine[119] to arginine ("G119R") and the second converts glutamate [117] to leucine, glycine[119] to arginine, and alanine[122] to aspartate (E117L, G119R, A122D).

The plasmids encoding these mutations as well as wild type bGH DNA (pBGHlOdelta) were transiently introduced into cultured mouse L cells, which were subsequently analyzed for bGH expression. Following "western analysis", protein bands of approximately 22,000 daltons were observed for wild type bGH and bGH derived from the two mutant genes.

Mouse L cells were maintained in DMEM (Gibco) plus 10% calf serum and 25 μ/ml gentamicin (Gibco). In this study, a modification of a previously described transfection procedure was employed (Lopata et al., Nucleic Acids Res., 12:5707-5717 (1984)). Briefly, 2 μg of plasmid DNA was added to 1.0 ml of DMEM containing 0.2mg DEAE-dextran. This solution was added to approximately 10⁶ cells in a 35-mm tissue culture plate which had been washed previously with 2.0ml of DMEM. Following incubation of the cells for 1 hour at 37° C., the DNA-DEAE-dextran solution was removed and the cells "shocked" for 90 seconds with 2.0ml of 10% DMSO in Hepes buffered saline, at room temperature. Subsequently, the "shock" solution was removed and cells washed with 2.0ml DMEM. Media containing 10% Nu-Serum (Collaborative Research) plus 50 μg/ml gentamicin were changed daily. Culture fluids were stored at −20° C. For bGH binding assays, transfected cells were incubated in DMEM minus serum for 16 hours, after which the culture fluids were removed and frozen at −20° C.

Sodium dodecyl sulfate (SDS) PAGE analyses of secreted bGH have been described (Kopchick et. al., DNA, 4:23-31 (1985); Kelder etl al., Gene, 76:75-80 (1989). In this study, we used a polyclonal anti-bGH serum for "western" analysis.

EXAMPLE 3

Growth Hormone Receptor Binding Studies

Culture fluids lacking serum were collected from cells transfected by pBGH-lOdelta6 (wild type bGH) and the mutant bGH concentration determinations, competitive membrane binding studies were carried out as previously described (Smith & Talamants, J. Bio. Chem., 262:2213-19 (1987)). Liver membrane preparations from C57BL/6JxSJL hybrid mice of either sex (60-120 days old) were homogenized with a Brinkman Polytron in 4 volumes (w/v) of 0.3M sucrose, 10nM EDTA, 50mM Hepes, 0.1nM TPCK and 1mM PMSF at pH 8.0. The above step and all the following protocols were carried out at 4° C. The homogenate was centrifuged at 20,000xg for 30 min. and the supernatant was centrifuged at 100,000xg for 1 hour. The pellets were washed once with 10nM Hepes, pH 8.0 and recentrifuged. These pellets were resuspended in 10mM Hepes, pH 8.0, to a protein concentration of approximately 50mg/ml. The membranes were aliquoted, frozen on dry ice, and stored at −20° C. Membrane protein concentrations were determined by the Lowry protein assay (Lowry et al., J. Biol. Chem., 193:265-275 (1951)).

Competitive binding assays were performed using the following protocol. Microsomal membranes corresponding to three mgs. protein were incubated with 30,000 cpm/tube [125]I bGH (Cambridge Medical Diagnostics) and unlabeled bGH ranging from 0.3ml assay buffer (20mM Hepes, 10mM CaCl₂ 0.1% BSA, and 0.05% NaN₃ pH 8.0). All assays were performed in triplicate. After overnight incubation at room temperature, membrane bound hormone was separated from free hormone by the addition of 1 ml of ice cold assay buffer followed by centrifugation at 10,000xg radioactivity. Specifically bound radioactivity was determined by subtraction from the value produced by incubation of membranes with 5 μg unlabled bGH (Smith and Talamants, 1987).

Effective doses which resulted in 50% displacement (ED50) of [125]I-bGH from the membrane preparations were determined. Mutant bGH encoded by pBGH-lOdelta6-G[119]R and pBGHlOdelta 6-E[117]L, G[119]R, $A^{122}D$ revealed an ED50 value similar to wild type bGH.

EXAMPLE 4

Transgenic Mouse Production Pilot Study

A series of transgenic mouse lines which contain wild type and mutant bGH genes were produced by standard microinjection techniques (McGrane et al., 1988). DNA extraction from mouse tails, dot blots, and serum determinations was as described (McGrane et al., 1988).

The genes contain the transcriptional regulatory sequences of the mouse metallothionein I promoter which has been shown to be active in liver tissue as well as other tissues of the transgenic mouse (Palmiter et al., Nature, 300:611-615 (1982)). Offspring generated by the microinjection procedure were assayed for bGH DNA by slot blot hybridization analysis. Mouse lines were generated which contain approximately one copy of the recombinant bGH DNA sequences derived from pBGH-lOdelta6, (wild type), pBGH-lOdelta6-$G^{119}R$, and pBGHlOdelta6-$E^{117}L$, $G^{119}R$, $A^{122}D$. Serum from transgenic animals were assayed for bGH levels by the Western technique. All mice which expressed the wild type bGH transgene in serum also possessed a corresponding enhanced growth rate. Mice which expressed mutant bGH ($G^{119}R$ or $E^{117}L$, $G^{119}R$, $A^{122}D$) in serum were dramatically and significantly smaller. After eight weeks' growth, the growth ratio for wild type bGH transgenic mice relative to control littermates was 1.5 while the ratio for the two bGH mutant mice to control littermates was −0.6. In the case of the triple mutant, we generated 10 founder mice that express the mutated bGH gene. The growth ratio between the transgenic and nontransgenic littermates ranged from 0.58 to 1.00. The degree of suppression of growth was directly related to the serum levels of the mutated bGH. Three founders have been bred that pass the trait to offspring; ≈50% of these offspring are positive for the gene and possess the corresponding small phenotype.

It has been demonstrated that many activities of GH are mediated through a family of peptides known as insulin-like growth factors (IGF), in particular IGF-1, which is believed to be produced primarily in the liver following GH binding to its receptor(s). (See Truesch, et al., Ann. Rev. Physiol., 47:44367 (1985); Zapt, et al., Harm. Res., 24:121-130 (1986)). IGF-1 has been shown to decrease GH production in the pituitary by a classical negative feedback mechanism. (Leung, et al., Endocrinology, 119:1489-96 (1986)). One hypothesis to explain the growth suppression in pBGH10 6-M8 transgenic mice is that bGH-M8 is active as an in vivo antagonist to mouse GH (mGH), thereby suppressing mouse IGF-1 production. If this is true, then one would expect not only a reduction in serum mouse IGF-1 levels in bGH M8 transgenic mice but also an increase in mGH production in the pituitary. We have found that the IFG-1 levels in the serum of the "small" transgenic mice are ~50% those of normal non-transgenic mice while mice containing wild type bGH (large mice) have approximately 2× the IGF-1 levels of non-transgenic mice. Results from immunoblot analysis of whole pituitary glands taken from bGH-M8 transgenic mice, bGH transgenic mice, and their nontransgenic littermates suggest that the pituitary glands in those growth-suppressed mice contain higher levels of mGH relative to their nontransgenic littermates. In contrast, mGH levels in bGH transgenic mice were largely depressed because mouse serum bGH1 levels were increased up to twice as much as levels in serum of their nontransgenic littermates. Palmiter, et al., Science, 222:809-14 (1983). Together, these results indicate that the altered bGH molecules are acting as an antagonist to endogenous mouse GH. Thus, it is the first example to our knowledge of an in vivo growth hormone antagonist and the first example of uncoupling of growth-promoting and receptor-binding activities of GHs.

EXAMPLE 5

Screening of other Muteins of bGH and hGH

By similar procedures, muteins of bGH and hGH with alterations in the third alpha helix have been prepared and tested for secretion in L cells, and, in selected cases, their effect on the growth of transgenic mice, with the following results.

The mutants are described by giving the original amino acid, its position in the amino acid sequence of bGH, and the replacement amino acid, with the amino acids set forth according to the internationally accepted single letter code. George, et al., Protein Seq. Data Anal., 1:27-39 (1987).

A first set of mutated bGH genes, when expressed in transgenic mice, resulted in animals with a growth ratio similar to that of mice which express wild type bGH (i.e., −1.59-1.72). We have referred these analogs as "full functional agonists" (Table I).

A second set of mutated bGH genes, when expressed in transgenic mice, resulted in mice with a growth ratio smaller than those animals which express wild type bGH (i.e., between 1.29-1.35). We refer to these bGH analogs as "partial functional agonists" and have listed them in Table II.

A third set of mutated bGH genes, when expressed in transgenic mice, resulted in animals with a growth ratio similar to nontransgenic mice (i.e., −1.0). We refer to these analogs as "non-functional agonists" (Table III).

A fourth set of mutated bGH genes, when expressed in transgenic mice, resulted in mice with a growth ratio of between 0.57 and 1.0 (Table IV). The growth ratio of the mice was negatively correlated with the serum level of the bgh analog, i.e., as the serum level of the bgh analog increased, the growth ratio of the animals decreased. This correlation is shown graphically in FIG. 13.

Also, these analogs, when expressed to NIH-3T3-preadipocytes, did not result in stimulation of preadipocytes differentiation; however, native GH will promote this differentiation (FIG. 12). In fact, these analogs will antagonize the ability of wildtype GH to promote preadipocyte differentiation (FIG. 11). We have referred to these analogs as "functional antagonists" (Table IV).

We have also generated transgenic mice which express either wild type hGH, hGH G120A, hgh G120R and hGH G120W (Table V). Mice which express hGH G120A show a growth enhanced phenotype similar to mice which express wild type hGH (Table V). We call this hGH analog a "functional angonist." In contrast, substitution of R or W for G at position 120 in hGH, and subsequent expression in transgenic mice, results in animals with a growth ratio between 0.73 and 0.96 (Table V), and whose level of serum hGH analogs is negatively correlated with the growth phenotype; i.e., as the serum levels of these hGH 120 analogs increase, the growth ratios decrease. This correlation is shown in FIG. 14. Therefore, like the bGH analogs which act as "functional antagonist," we termed these hGH 120 analogs as "functional antagonist." It is important to note that the glycine residue in bGH at position 119 is the homologue of the glycine residue in hGH at position 120. They are both located in the central portion of the third α-helix.

A subset of bGH analogs is presented in Table VI in which we have evaluated their ability to be secreted following transfection of the mutated DNA into mouse L cells. Transgenic animals have not been generated which contain these mutated DNAs.

The mutant K112L, K114W shows the effect of expanding the hydrophobic face of the helix. This mutant affects animal growth much as does wild type growth hormone.

The mutations K114P, E118P and L121P (and various combinations thereof) apparently destroy the alpha helix (Proline is a strong alpha helix breaker.) The growth-related biological activity is abolished. The mutation E126G is a special case; glycine is a helix breaker, but position 126 is at the end of the helix so the normal biological activity is retained. With G119P, however, one strong helix breaker was substituted for an even strong one; the alpha helix was apparently preserved.

The third alpha helix of wild type growth hormone diverges from a perfect amphiphilic alpha helix at three positions. First, at 117, Glu is a hydrophilic amino acid in the hydrophobic face. Second, at 119, Gly is a neutral amino acid in the hydrophilic face. Finally, at 122, Ala is a hydrophobic amino acid in the hydrophilic face. The mutations E117L, G119R and A122D, separately or in combination, increase the amphiphilic character of the helix. G119R additionally increases the alpha-helical tendencies of the sequence.

Our initial hypothesis was that the growth-inhibitory activity of the mutants G119R and E117L/G119-R/A122D was associated with the increased amphipathicity of the third alpha helix. We have since developed evidence that the amphipathicity of the third alpha helix is largely irrelevant to that activity.

(1) The single E117L, like wt bGH, produced large animals.
(2) Mutant G119P produced the small animal phenotype even though proline is as hydrophilic as glycine.
(3) Mutant G119L produced the small animal phenotype even though leucine is hydrophobic nd therefore disrupts the hydrophilic face of the helix.
(4) Mutant E111L/G119W/R125L produced the small animal phenotype even though all three mutations disrupt the hydrophilic face of the helix.
(5) The single A122D produces a mutein which has no effect on growth.

Thus, in one embodiment, the present invention relates to mutations of the third alpha helix which result in growth-inhibitory activity yet reduce or leave unchanged the amphiphilic character of the helix.

Additional growth hormone antagonists may be identified by systematically varying the codon corresponding to G119 in bGH, so as to express the 18 other mutants having a single amino acid change at this position. This is readily accomplished by synthesizing oligonucleotides differing from those set forth in Example 1 at codon 119 so as to encode the desired alternative amino acid. Similarly, one may alter the homologous glycine reside in the third alpha helix of other GHs, e.g., the $G^{120}$ of hGH. By similar means, variations of the codons corresponding to other amino acids of the third alpha helix of a GH are investigated.

EXAMPLE 6

Anticholesterolemic Activity of Growth Hormone Antagonists

Procedures for Clinical Chemistry Tests

Blood samples were obtained from mouse tails. The samples were allowed to clot at room temperature for 5 minutes and were then centrifuged and the serum was collected and frozen at $-20°$ C. until analysis. Total Cholesterol (TC) Triglyceride (TR), Glucose (GL), and Blood Urea Nitrogen (BUN) were analyzed on a Kodak Ektachem DT 60 Analyzer using dry, multilayered, self-contained elements specific for each test. 10 µl of serum was pipetted on individual slides specific for each test and were analyzed using colorimetric measurement by reflectance spectrophotometry methods and compared to daily Quality Control reference samples.

Results

There is no significant difference in blood glucose, serum urea/nitrogen and serum triglyceride levels between bGHM8 transgenic mice and their nontransgenic littermates. However, total serum cholesterol levels in bGH-M8 transgenic mice are significantly decreased ($P<0.05$) as compared to their nontransgenic littermates and bGH transgenic mice.

EXAMPLE 7

In Vitro Bioassay for Growth Hormone Antagonist Activity

Studies of growth hormone have shown that it promotes the formation of adipose from preadipose 3T3 cells. Murikawa, et al., Cell 29:789 (1982). Glycerophosphate dehydrogenase (GPDH) has been used as a differentiation marker for this GH induced adipose conversion. Wise and Green, J. Biol. Chem., 254:273-75 (1979); Nixon and Green, Endocrinology, 114:527 (1984); Pairault and Green, Proc. Nat. Acad. Sci. (USA) 76:5138 (1979).

We have adapted this assay to determine whether a bGH mutant acts as a GH antagonist. Both bGH and bGH-M8 bind to receptors on these preadipocytes with a Kd value of 10mM. When exposed to native sequence bovine growth hormone (30 pM) and cultured for seven days, the preadipocytes differentiate and GPDH activity is stimulated. If the bGH mutant is added to culture medium containing wild-type bGH, there is a dose dependent reduction in GPDH activity and therefore, presumably, in adipose conversion (FIG. 11).

This assay is a convenient screening tool for identifying potential GH antagonists.

EXAMPLE 8

Mice transgenic for the wild type bGH gene are known to develop progressive severe glomerulosclerosis and increased glomerular size. Doi, et al., Am. J. Path., 137: 541-52 (199); Resce, et al., Lab. Invest., 65: 601-5 (1991); Doi, et al., Am. J. Path., 131: 398-403 (1988); see also Stewart, et al., Endocrinology, 130: 405-414 (1992). This is not merely a function of body size, as bGH-M11 mice (i.e., L121P, E126G mutants), those mutant bGH does not enhance growth, also exhibit glumerulosclerosis. In bGH-M8 (G119R) mice, however, which had reduced serum IGF-1, body size, and glomerular size relative to nontransgenic mice, glomerulosclerosis was absent.

Summary of growth ratio comparisons between transgenic mice expressing bGH analogs and their non-transgenic littermates at 6 to 8 weeks of age.

TABLE 1

Transgenic mice which express the following bGH analogs exhibited phenotypes similar to transgenic mice which express wild type bGH (we have termed these analogs "full functional agonists")*

| bGH Analogs | n | Mean Growth Ratio | SD |
| --- | --- | --- | --- |
| WT-bGH | 7 | 1.61 | 0.14 |
| bGH-111A | 2 | 1.72 | — |
| bGH-K112L | 12 | 1.70 | 0.19 |
| bGH-K114W | 12 | 1.70 | 0.19 |
| bGH-L116A | 6 | 1.71 | 0.16 |
| bGH-E117L | 13 | 1.68 | 0.18 |
| bGH-A122T | 10 | 1.67 | 0.16 |
| bGH-R125L | 3 | 1.61 | 0.18 |
| bGH-E126G | 4 | 1.59 | 0.14 |

*There is no correlation between serum levels of these bGH analogs and the growth phenotypes. These mutated bGH genes are expressed in mouse L cells and the secretion pattern is similar to the wild type bGH.

TABLE II

Transgenic mice which express the following bGH analogs exhibited phenotypes smaller than transgenic mice which express wild type bGH, however, large than non-transgenic mice (we have termed these analogs "partial functional agonists")*

| bGH | n | Mean Growth Ratio | SD |
| --- | --- | --- | --- |
| WT-bGH | 7 | 1.61 | 0.14 |
| D115A | 3 | 1.35 | 0.15 |
| L123I | 3 | 1.29 | 0.13 |

*There is no correlation between serum levels of these bGH analogs and the growth phenotypes. These mutated bGH genes are expressed in and secreted by mouse L cells with the pattern similar to wild type bGH.

Note that for the purposes of Tables I–VI, the characterization of a mutein as "functional" or "non-functional" is in the context of its effect on growth.

TABLE III

Transgenic mice which express the following bGH analogs exhibited phenotypes similar to their non-transgenic littermates (we have termed these analogs as "non-functional agonists")*

| bGH Analogs | n | Mean Growth Ratio | SD |
| --- | --- | --- | --- |
| K114P,E118P | 9 | 1.01 | 0.09 |
| L121P,E126G | 11 | 0.94 | 0.06 |
| A122D | 9 | 0.90 | 0.11 |

*There is no correlation between levels of bGH analogs in serum and the growth phenotypes. These mutated bGH genes are expressed in and secreted by mouse L cells with the exceptions of bGH-K114P,E118P and bGH-L121P,E126G which are not secreted by mouse L cells.

TABLE IV

Transgenic mice which express the following bGH analogs exhibited phenotypes smaller than non-transgenic littermates (we have termed these analogs as "functional antagonists")*

| bGH Analogs | Animal # | Sex | Serum bGH (ug/ml) | Growth Ratio (Two Month) |
| --- | --- | --- | --- | --- |
| E117L,G119R, A122D | 6 | F | 3.4 | 0.58 |
| | 15 | M | 3.3 | 0.69 |
| | 32 | F | 3.7 | 0.57 |
| | 51 | F | 5.1 | 0.63 |
| | 55 | M | 2.1 | 0.85 |
| | 65 | F | 0.6 | 1.0 |
| | 67 | F | 0.6 | 0.87 |
| | 70 | F | 3.3 | 0.70 |
| | 71 | F | 2.6 | 0.70 |
| | 89 | F | 1.8 | 0.85 |
| G119R | 25 | M | 0.5 | 0.93 |
| | 28* | M | 0.9 | 0.88 |

TABLE IV-continued

Transgenic mice which express the following bGH analogs exhibited phenotypes smaller than non-transgenic littermates (we have termed these analogs as "functional antagonists")*

| bGH Analogs | Animal # | Sex | Serum bGH (ug/ml) | Growth Ratio (Two Month) |
| --- | --- | --- | --- | --- |
| | 49* | M | 6.0 | 0.60 |
| | 53 | M | 1.5 | 0.85 |
| | 94 | F | 0.2 | 0.98 |
| | 138 | F | 3.0 | 0.74 |
| G119P | 9 | F | 2.0 | 0.81 |
| G119K | 10 | M | 0.5 | 0.84 |
| | 12 | M | 0.4 | 0.95 |
| | 18 | F | 4.0 | 0.78 |
| | 26 | F | 5.0 | 0.59 |
| G119L | 23 | F | 6.5 | 0.81 |
| | 27 | M | 0.5 | 1.0 |
| G119W | 16 | M | 8.0 | 0.64 |
| G119Δ | 14 | M | 0.5 | 0.96 |
| | 15 | M | 0.5 | 0.90 |
| | 22 | M | 8.0 | 0.75 |
| | 23 | M | 0.5 | 0.90 |

*The level of mouse growth suppression is correlated with serum levels of analogs (see FIG. 13). These mutated bGH genes are expressed in and secreted mouse L cells. The secretion pattern is similar to wild type bGH.

TABLE V

Summary of transgenic mice which express hGH genes encoding single amino acid substitutions at position 120* (hGH-G120A is a "full-functional agonist". hGH-G120R and hGH-G120W serve as "functional antagonists")

| hGH Analogs | Animal # | Sex | Serum hGH (ug/ml) | Growth Ratio (Two Months) |
| --- | --- | --- | --- | --- |
| WT-hGH | n = 7 | | | 1.62 ± 0.15 |
| G120A | 95 | M | 3.9 | 1.48 |
| | 6 | F | 21.5 | 1.76 |
| G120R | 20 | F | 78.5 | 0.79 |
| | 48 | F | 1.5 | 0.96 |
| | 68 | M | 3.4 | 0.73 |
| | 73 | F | 0.8 | 0.93 |
| | 92 | F | 1.1 | 0.93 |
| G120W | 18 | M | 5.5 | 0.82 |
| | 39 | M | 2.7 | 0.77 |
| | 56 | F | 2.0 | 0.83 |

*bGH Gly 119 is in a position equivalent to hGH Gly 120. Therefore, we refer to hGH Gly 120 consistently with the literature.
**The level of growth suppression is correlated with serum levels of hGH analogs (see FIG. 14)

TABLE VI

Summary of mutated bGH genes expressed in mouse L cell without transgenic mice dats.

| bGH Analogs | L-Cell Secretion |
| --- | --- |
| Wild type bGH | + |
| K114P | — |
| E118P | — |
| E117,G119R | + |
| E117,A122D | + |
| V109D,Y110D,L116R | + |
| E111L,G119W | + |
| L121R,M124K | + |
| E111L,G119W,L121R,M124K | + |
| D115V | + |
| D115G | + |
| V109D,Y111D,L116R,L121R,M124K | — |
| E111L,G119W,R125L[1] | + |
| E111L,G119W,L121R,M124K | + |
| V109D,Y110D,L116K,R125L | + |

[1]This bGH Analog resulted in a Mean Animal Transgenic/Nontransgenic Growth Ratio of 0.7.

TABLE VII

| "M" mice mutants | |
| --- | --- |
| M1 | (K112L,K114W) |
| M10 | (K114P,E118P) |
| M11 | (L121P,E126G) |

TABLE VII-continued

| "M" mice mutants | |
|---|---|
| M4 | (E117L) |
| M6 | (G119R) |
| M2 | (A122D) |
| M7 | (E117L,G119R) |
| M3 | (E117L,A122D) |
| M8 | (E117L,G119R,A122D) |

We hereby claim:

1. A vertebrate growth hormone in which the amino acid position in said vertebrate growth hormone corresponding to amino acid Gly 119 of bovine growth hormone is deleted or substituted with an amino acid, said vertebrate growth hormone having growth hormone antagonist activity.

2. The vertebrate growth hormone of claim 1 in which the amino acid position in said vertebrate growth hormone corresponding to amino acid Gly 119 of bovine growth hormone is substituted with an amino acid selected from the group consisting of Arg, Trp, Pro, Lys and Leu.

3. The vertebrate growth hormone of claim 2, in which said substitution is with Arg.

4. The vertebrate growth hormone of claim 1, 2, or 3, wherein said vertebrate growth hormone is a mammalian growth hormone.

5. The vertebrate growth hormone of claim 1, wherein there is a deletion at the amino acid position corresponding to amino acid Gly 119 of bovine, growth hormone.

6. The vertebrate growth hormone of claim 1, wherein said vertebrate growth hormone is selected from the group consisting of flounder, yellowtail, tuna, salmon, chicken, rat, porcine, ovine, bovine and human growth hormones.

7. A vertebrate growth hormone in which there are two substitutions or deletions at amino acid positions corresponding to the amino acid positions of bovine growth hormone, said substitutions or deletions at Gly 119 and at an amino acid position selected from the group consisting of Ala 122, Leu 123, Ile 120, Leu 116, Asp 115 and Glu 118, said vertebrate growth hormone having growth hormone antagonist activity.

8. The vertebrate growth hormone of claim 7, wherein the amino acid substitution at the amino acid position corresponding to Asp 115 of bovine growth hormone is selected from the group consisting of His, Met, Ile, Leu, Lys, Arg, Phe, Tyr and Trp.

9. The vertebrate growth hormone of claim 7, wherein the vertebrate growth hormone is a mammalian growth hormone.

10. Human growth hormone in which amino acid Gly 120 is deleted or substituted with an amino acid, said human growth hormone having growth hormone antagonist activity.

11. The human growth hormone of claim 10 in which amino acid Gly 120 is substituted with an amino acid selected from the group consisting of Arg, Trp, Pro, Lys and Leu.

12. The human growth hormone of claim 11 in which amino acid Gly 120 is substituted with Arg.

13. The human growth hormone of claim 11 in which amino acid Gly 120 is substituted with Trp.

14. The human growth hormone of claim 10 in which amino acid Gly 120 is deleted.

15. Human growth hormone wherein the amino acid position corresponding to amino acid Glu 117 of bovine growth hormone is substituted with Leu, the amino acid position corresponding to amino acid Gly 119 of bovine growth hormone is substituted with Arg and the amino acid position corresponding to amino acid Ala 122 of bovine growth hormone is substituted with Asp, said human growth hormone having growth hormone antagonist activity.

16. Human growth hormone in which there are two substitutions or deletions at amino acid positions corresponding to the amino acid positions of bovine growth hormone, said substitutions or deletions at Gly 119 and at an amino acid position selected from the group consisting of Ala 122, Leu 123, Ile 120, Leu 116, Asp 115 and Glu 118, said human growth hormone having growth hormone antagonist activity.

17. The human growth hormone of claim 16, in which the substitution at the amino acid position corresponding to amino acid Asp 115 of bovine growth hormone is selected from the group consisting of His, Met, Ile, Leu, Lys, Arg, Phe, Tyr and Trp.

18. Human growth hormone wherein the amino acid position corresponding to amino acid Glu 111 of bovine growth hormone is substituted with Leu, the amino acid position corresponding to amino acid Gly 119 of bovine growth hormone is substituted with Trp and amino acid position corresponding to amino acid Arg 125 of bovine growth hormone is substituted with Leu, said human growth hormone having growth hormone antagonist activity.

19. Bovine growth hormone in which amino acid Gly 119 is deleted or substituted with an amino acid, said bovine growth hormone having growth hormone antagonist activity.

20. The bovine growth hormone of claim 19 in which amino acid Gly 119 is substituted with an amino acid selected from the group consisting of Arg, Trp, Pro, Lys and Leu.

21. The bovine growth hormone of claim 20 in which amino acid Gly 119 is substituted with Arg.

22. The bovine growth hormone of claim 19 in which amino acid Gly 119 is deleted.

23. Bovine growth hormone wherein amino acid Glu 117 is substituted with Leu, amino acid Gly 119 is substituted with Arg and amino acid Ala 122 is substituted with Asp, said bovine growth hormone having growth hormone antagonist activity.

24. Bovine growth hormone in which there are two substitutions or deletions, said substitutions or deletions at amino acid position Gly 119 and at an amino acid position selected from the group consisting of Ala 122, Leu 123, Ile 120, Leu 116, Asp 115 and Glu 118, said bovine growth hormone having growth hormone antagonist activity.

25. The bovine growth hormone of claim 24, in which the substitution at amino acid Asp 115 is selected from the group consisting of His, Met, Ile, Leu, Lys, Arg, Phe, Try and Trp.

26. Bovine growth hormone wherein amino acid Glu 111 is substituted with Leu, amino acid Gly 119 is substituted with Trp and amino acid Arg 125 is substituted with Leu, said bovine growth hormone having growth hormone antagonist activity.

27. A pharmaceutical composition comprising a compound of claim 1, 2, 3, 4, 5, 6, 7, 8, 9, 10, 11, 12, 13, 14, 15, 16, 17, 18, 19, 20, 21, 22, 23, 24, 25, or 26 and a pharmaceutically acceptable carrier.

* * * * *

UNITED STATES PATENT AND TRADEMARK OFFICE
CERTIFICATE OF CORRECTION

PATENT NO. : 5,350,836

DATED : September 27, 1994

INVENTORS : JOHN J. KOPCHICK AND WEN Y. CHEN

Page 1 of 3

It is certified that error appears in the above-identified patent and that said Letters Patent is hereby corrected as shown below:

Column 1, line 5, "1191" should read --1991--; line 40, "(yeast;" should read --(yeast);--; line 42, "(bacterial)" should read --(bacteria)--; line 47, "GB 3,073,245" should read --GB 2,073,245--.
    Column 2, line 40, "inn" should read --in--.
    Column 4, line 12, "in" should read --is--; line 26, "PBGH10Δ6" should read --pBGH10Δ6--.
    Column 5, line 22, "GDPH" should read --GPDH--; line 52, "grown" should read --growth--; line 68, "rate" should read --rat--.
    Column 6, line 4, "rate" should read --rat--; line 39, "160" should read --106--; line 46, "Sonenber" should read --Sonenberg--; line 63, "pGH oGH" should read --pGH, oGH--.
    Column 7, line 5, "Four" should read --Five--; line 7, "Asp 12" should read --Asp 129--; line 43, "non" should read --none--.
    Column 8, line 8, "growth in" should read --growth hormone in--; line 26, "or" should read --of--; line 39, "largen" should read --larger--; line 46, "(G119r" should read --(G119R--.
    Column 10, line 46, "(GH" should read --GH--; line 56, ""hormonephage"" should read --"hormone phage"--; line 57, "displayh GH-geneIII" should read --display hGH-geneIII--.
    Column 12, line 39, "cycteines" should read --cysteines--; line 49, "Thr in yGH and tGH, Val in sGH." should read --Thr in yGH and tGH. The third is replaced by Leu in fGH, Ile in yGH and tGH, Val in sGH.--.
    Column 14, line 52, "they" should read --then--.

UNITED STATES PATENT AND TRADEMARK OFFICE
CERTIFICATE OF CORRECTION

PATENT NO. : 5,350,836

DATED : September 27, 1994

INVENTOR(S) : John J. Kopchick and Wen Y. Chen

Column 16, line 25, the oligonucleotide sequence "GAATCCTGGCCTGATGCGGGAGCTGGA" should read --GATCCTGGCCCTGATGCGGGAGCTGGA--; line 28, the oligonucleotide sequence "GCAT  CAGGGCCAGGATCCTTTCCT" should read --GCATCAGGGCCAGGATCCTTTCCT--; line 29, the oligonucleotide sequence "CCAGGTCCTTCAGCTTCTCATAGAC" should read --CCAGGTCCTTCAGCTTCTCATAGACA--; line 37, the oligonucleotide sequence "ATCCAGGTCCAGGATCCTTTCCAG" should read --ATCAGGTCCAGGATCCTTTCCAG--; below line 39, in the hybridized oligonucleotides coding for E117L, G119R, A122D, at Leu 117, in the 3'→ 5' nucleotide sequence, "GTC" should read --GAC--; at Asp 122, in the 3'→ 5' nucleotide sequence, "CGG" should read --CTG--; line 67, delete "acid".

Column 18, line 30, "and the mutant bGH concentration determinations," should read --and the mutant bGH genes. Following lyophilization of the culture media and bGH concentration determinations,-; line 36, "10nM" should read --10mM--; line 37, "0.1nM TPCK" should read --0.1mM TPCK--; line 42, "10nM Hepes," should read --10mM Hepes--; lines 59-60, "10,000xg radioactivity." should read --10,000xg for 20 min. Membrane pellets were then assayed for radioactivity.--.

Column 21, line 48, "nd" should read --and--.

UNITED STATES PATENT AND TRADEMARK OFFICE
CERTIFICATE OF CORRECTION

PATENT NO. : 5,350,836

DATED : September 27, 1994

INVENTOR(S) : John J. Kopchick and Wen Y. Chen

It is certified that error appears in the above-indentified patent and that said Letters Patent is hereby corrected as shown below:

Column 22, line 62, "(199)" should read --(1990)--; line 67 "those" should read --whose--.

In claim 5, at column 25, line 30, "bovine, growth" should read --bovine growth --.

Signed and Sealed this

Twenty-first Day of February, 1995

Attest:

BRUCE LEHMAN

Attesting Officer     Commissioner of Patents and Trademarks